United States Patent
Kendall et al.

(10) Patent No.: US 7,713,473 B2
(45) Date of Patent: May 11, 2010

(54) STERILIZATION SYSTEM AND VAPORIZER THEREFOR

(75) Inventors: Richard Jed Kendall, San Clemente, CA (US); James P. Kohler, Laguna Hills, CA (US); Szu-Min Lin, Irvine, CA (US)

(73) Assignee: Ethicon, Inc., Somerville, NJ (US)

( * ) Notice: Subject to any disclaimer, the term of this patent is extended or adjusted under 35 U.S.C. 154(b) by 193 days.

(21) Appl. No.: 11/172,522

(22) Filed: Jun. 30, 2005

(65) Prior Publication Data

US 2007/0003431 A1   Jan. 4, 2007

(51) Int. Cl.
- *A61L 2/00* (2006.01)
- *F22B 27/00* (2006.01)
- *F22B 1/28* (2006.01)
- *F22B 1/20* (2006.01)
- *B05B 3/16* (2006.01)

(52) U.S. Cl. .................. 422/28; 422/300; 392/399; 392/386; 392/394; 239/136

(58) Field of Classification Search .............. 422/38, 422/305, 28; 122/40; 392/386, 394, 399; 261/DIG. 65; 239/136; 203/90
See application file for complete search history.

(56) References Cited

U.S. PATENT DOCUMENTS

| | | | |
|---|---|---|---|
| 2,491,732 A | 12/1949 | Hawkinson | |
| 3,211,633 A * | 10/1965 | Hammer et al. | 202/236 |
| 3,244,601 A | 4/1966 | Gunther | |
| 3,351,119 A | 11/1967 | Rosenblad | |
| 4,643,867 A | 2/1987 | Hornak et al. | |
| 4,704,254 A | 11/1987 | Nichols | |
| 4,898,713 A | 2/1990 | Picard | |
| 4,909,999 A | 3/1990 | Cummings | |
| 5,078,976 A * | 1/1992 | Shibauchi et al. | 422/298 |
| 5,098,518 A | 3/1992 | Sakai | |
| 5,445,792 A * | 8/1995 | Rickloff et al. | 422/28 |
| 5,851,485 A | 12/1998 | Lin et al. | |
| 5,887,117 A * | 3/1999 | Desu et al. | 392/386 |
| 6,106,772 A | 8/2000 | Kohler et al. | |
| 6,365,102 B1 | 4/2002 | Wu et al. | |
| 6,379,631 B1 | 4/2002 | Wu | |
| 6,734,405 B2 * | 5/2004 | Centanni et al. | 219/628 |
| 7,014,813 B1 * | 3/2006 | Watling et al. | 422/26 |
| 2002/0068012 A1 | 6/2002 | Platt, Jr. et al. | |

(Continued)

FOREIGN PATENT DOCUMENTS

EP   243003 A2   10/1987

(Continued)

OTHER PUBLICATIONS

English Translation of Japanese Publication No. 2005-065882A: Inaba et al., Vaporization Apparatus of Sterilization liquid for food containers, has heating surface inclined at predetermine angle, and nozzle for dripping sterilization liquid to heating surface, such that evaporation vaporization is performed, Mar. 17, 2005.*

(Continued)

*Primary Examiner*—Sean E Conley
*Assistant Examiner*—Kevin C Joyner

(57) ABSTRACT

A sterilizer employs a vaporizer having sloped surfaces over which flow liquid sterilant solution for vaporization. The arrangement promotes even distribution of the sterilant solution for more efficient vaporization.

12 Claims, 25 Drawing Sheets

U.S. PATENT DOCUMENTS

2005/0084415 A1* 4/2005 McVey et al. .................. 422/28

FOREIGN PATENT DOCUMENTS

| EP | 1378250 | A1 |   | 1/2004 |
|----|---------|----|---|--------|
| GB | 880404 | A |   | 10/1961 |
| GB | 2089226 | A |   | 6/1982 |
| JP | 09294805 | A | * | 11/1997 |
| JP | 2005065882 | A | * | 3/2005 |
| WO | WO 2004036137 | A2 |   | 4/2004 |

OTHER PUBLICATIONS

Advanced Sterilization Products, U.S. Appl. No. 09/728,973, pending.

European Search Report dated Aug. 2, 2007.

* cited by examiner

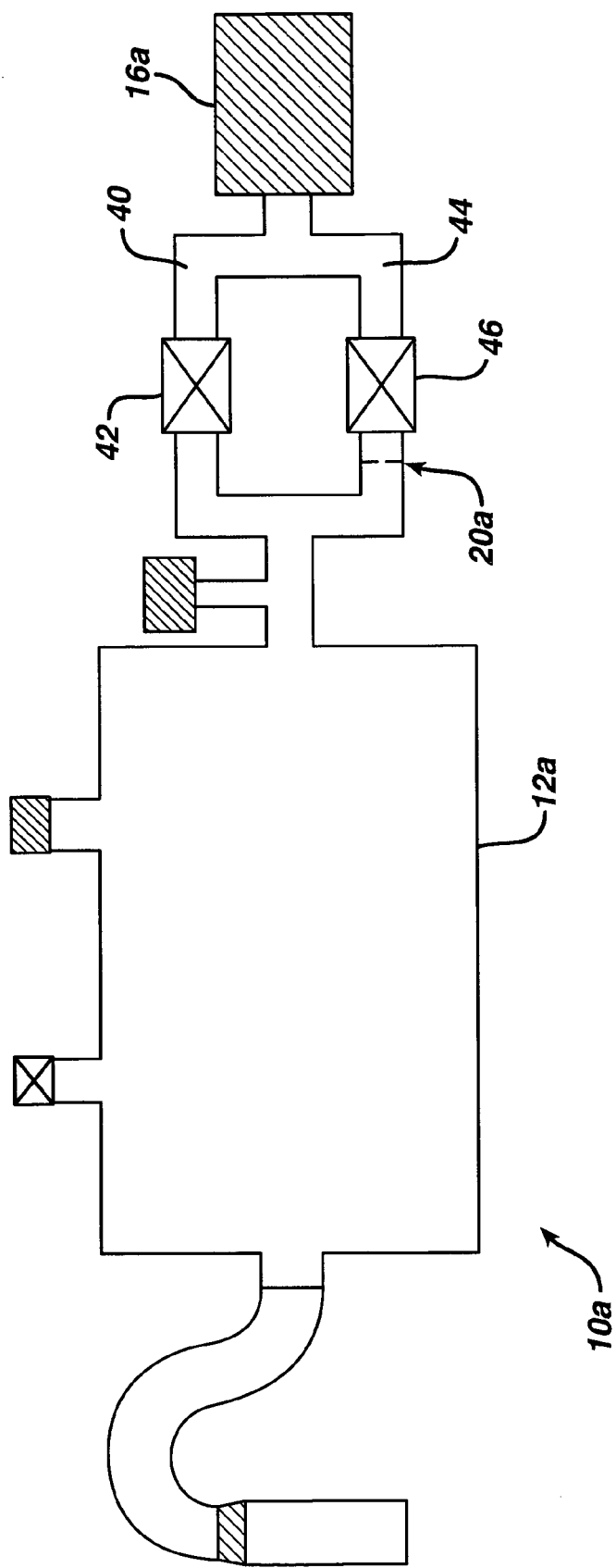

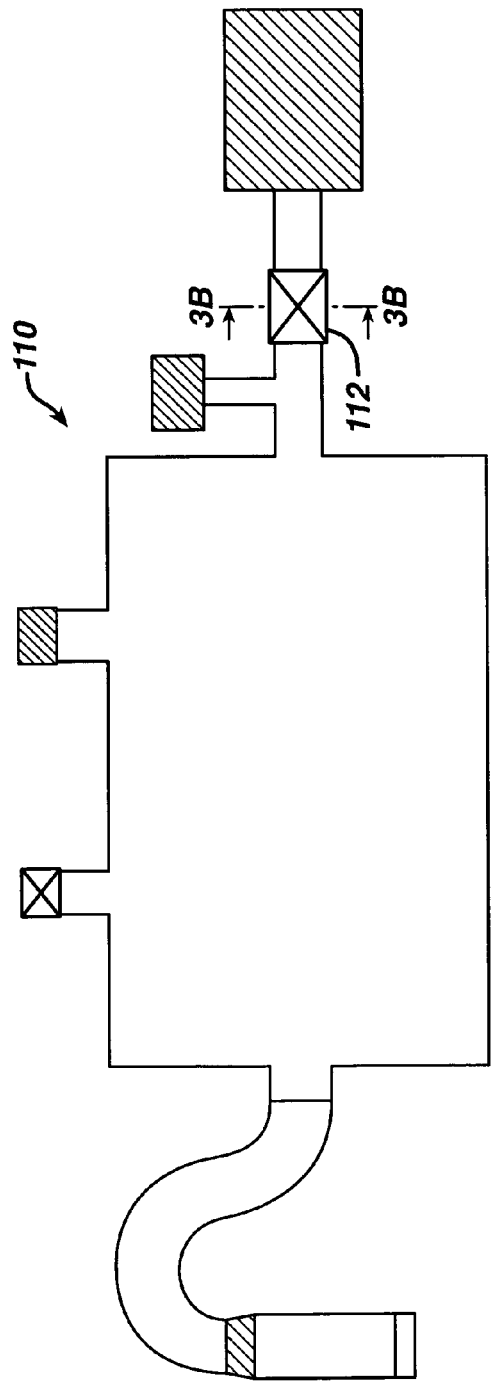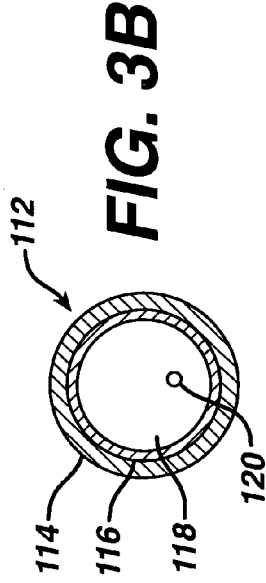

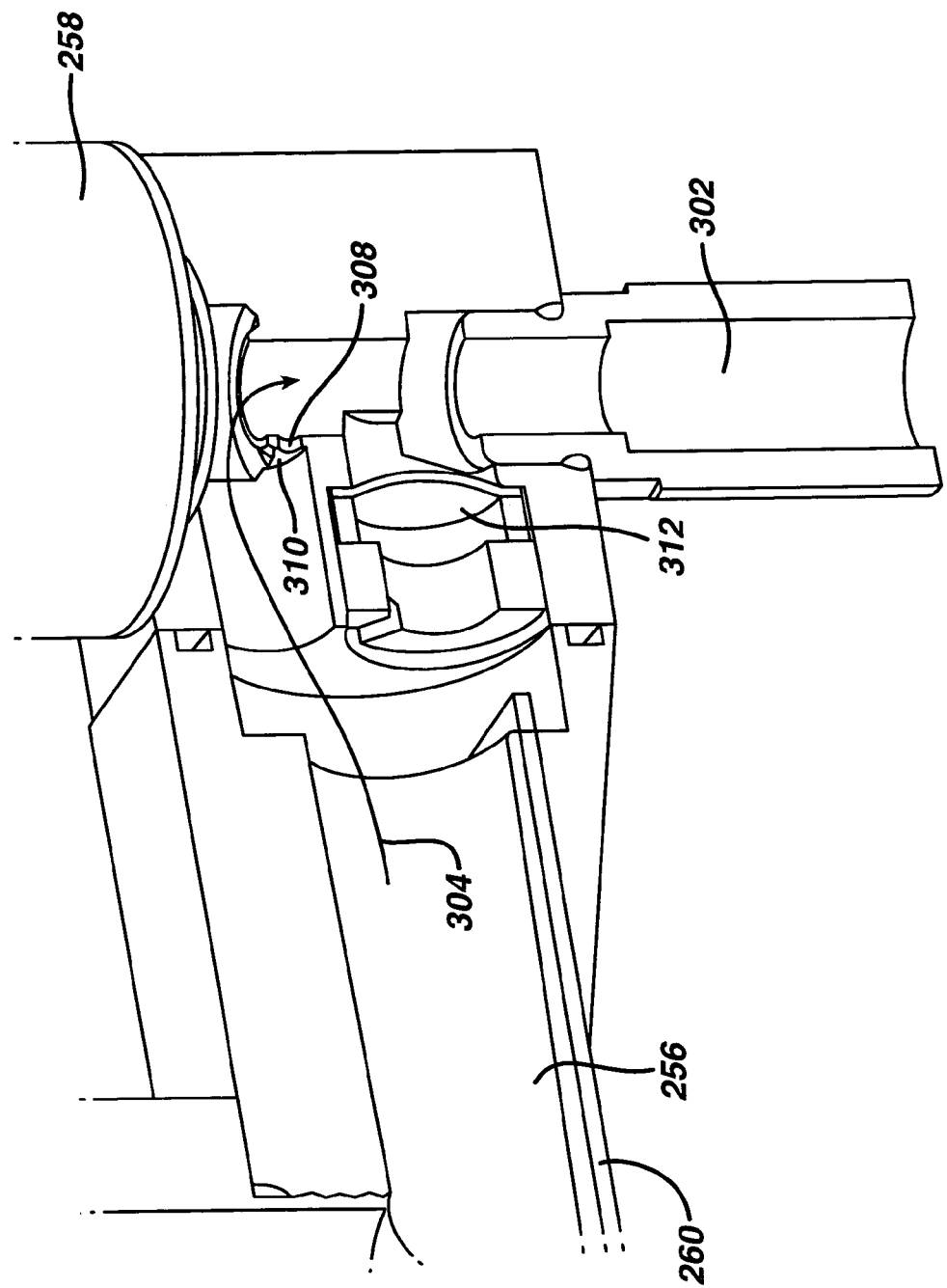

STERILIZATION SYSTEM AND VAPORIZER THEREFOR

FIELD OF THE INVENTION

The invention relates to sterilization of articles, and more particularly to vaporization of a liquid sterilant solution to provide a sterilant vapor.

BACKGROUND OF THE INVENTION

It is known to sterilize articles with a vaporized chemical sterilant, such as hydrogen peroxide, peracetic acid and glutaraldehyde. Wu et al. U.S. Pat. No. 6,365,102, incorporated herein by reference, describes a hydrogen peroxide/gas plasma sterilization system comprising a vacuum chamber, source of hydrogen peroxide vapor and a source of RF energy to create a plasma. Such systems marketed under the name STERRAD® are available from Advanced Sterilization Products division of Ethicon, Inc. in Irvine, Calif.

Rapid and efficient vaporization of a liquid sterilant solution to produce the sterilant vapor speeds the overall sterilization process, ensures complete vaporization and ensures that the vaporization phase of a sterilization cycle completes in a timely and repeatable fashion.

SUMMARY OF THE INVENTION

The present invention improves the speed with which a sterilization cycle can be completed.

A method, according to the present invention, provides a vapor phase sterilant to a sterilizing chamber. The method comprises the steps of: heating a vaporizing surface, the vaporizing surface being inclined; flowing a liquid sterilant solution over the vaporizing surface causing the sterilant solution to vaporize into a sterilant vapor; and delivering the sterilant vapor to the sterilization chamber.

In one aspect of the invention, the vaporizing surface has a plurality of downwardly running channels and the sterilant solution, while flowing over the surface, runs down the channels.

In one aspect of the invention the liquid sterilant solution is sprayed onto the vaporizing surface, preferably onto an upper half of the vaporizing surface.

In one aspect of the invention, the vaporizing surface comprises a first face and a second face which join at upper extents thereof, with a portion of the liquid sterilant solution flowing over the first face and another portion of the liquid sterilant solution flowing over the second face.

Preferably, the liquid sterilant solution comprises hydrogen peroxide and water.

In one aspect of the invention, the vaporizing surface comprises a plurality of wells which capture portions of the liquid sterilant solution as it flows down the vaporizing surface and hold these portions until they are vaporized. Preferably, the individual volume of the portions captured within the wells is between 10 and 50 micro liters.

In one aspect of the invention, the vaporizing surface comprises a plurality of protuberances wherein to increase its surface area.

Preferably, the vaporizing surface is inclined at an angle of between 15 to 60 degrees with respect to horizontal, and more preferably at an angle of between 25 to 50 degrees with respect to horizontal.

A sterilization system, according to the present invention, comprises a sterilization chamber and a vaporizer for supplying a vapor phase chemical sterilant to the sterilization chamber. The vaporizer comprises a vaporizing surface which is inclined with respect to horizontal. A means is provided for heating the vaporizing surface and a further means is provided for flowing a liquid sterilant solution onto the vaporizing surface. A passage between the vaporizer and the sterilization chamber provides for pathway for supplying the vaporized sterilant to the sterilization chamber.

Preferably, the means for flowing a liquid sterilant solution onto the vaporizing surface comprises a nozzle whereby the liquid sterilant solution is sprayed onto the vaporizing surface. More preferably, the nozzle is directed so that a majority of the liquid sterilant solution is sprayed onto an upper half of the vaporizing surface.

A plurality of ports can be provided for directing liquid sterilant over the vaporizing surface.

BRIEF DESCRIPTION OF THE DRAWINGS

FIG. 3 is a block diagram of an alternate embodiment of a sterilization system according to the present invention;

FIG. 3A is a block diagram of an alternative embodiment of a sterilization system according to the present invention.

FIG. 3B is a sectional view taken along lines 3B-3B of FIG. 3A;

FIG. 14A is a close-up section view of the valve assembly shown in FIG. 14;

DETAILED DESCRIPTION

Figure 1:
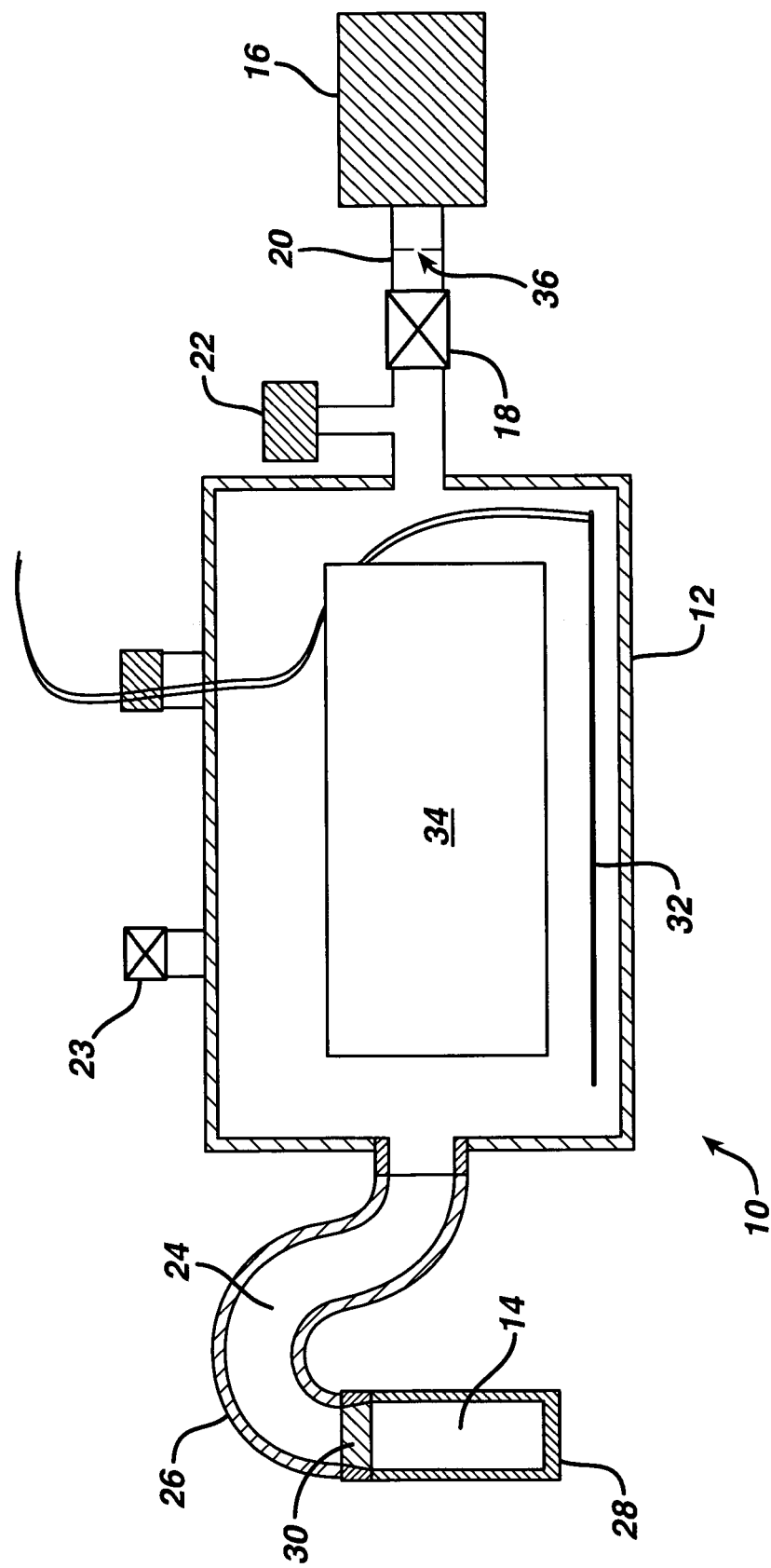
FIG. 1 is a block diagram of a sterilization system according to the present invention.
Figure 2:
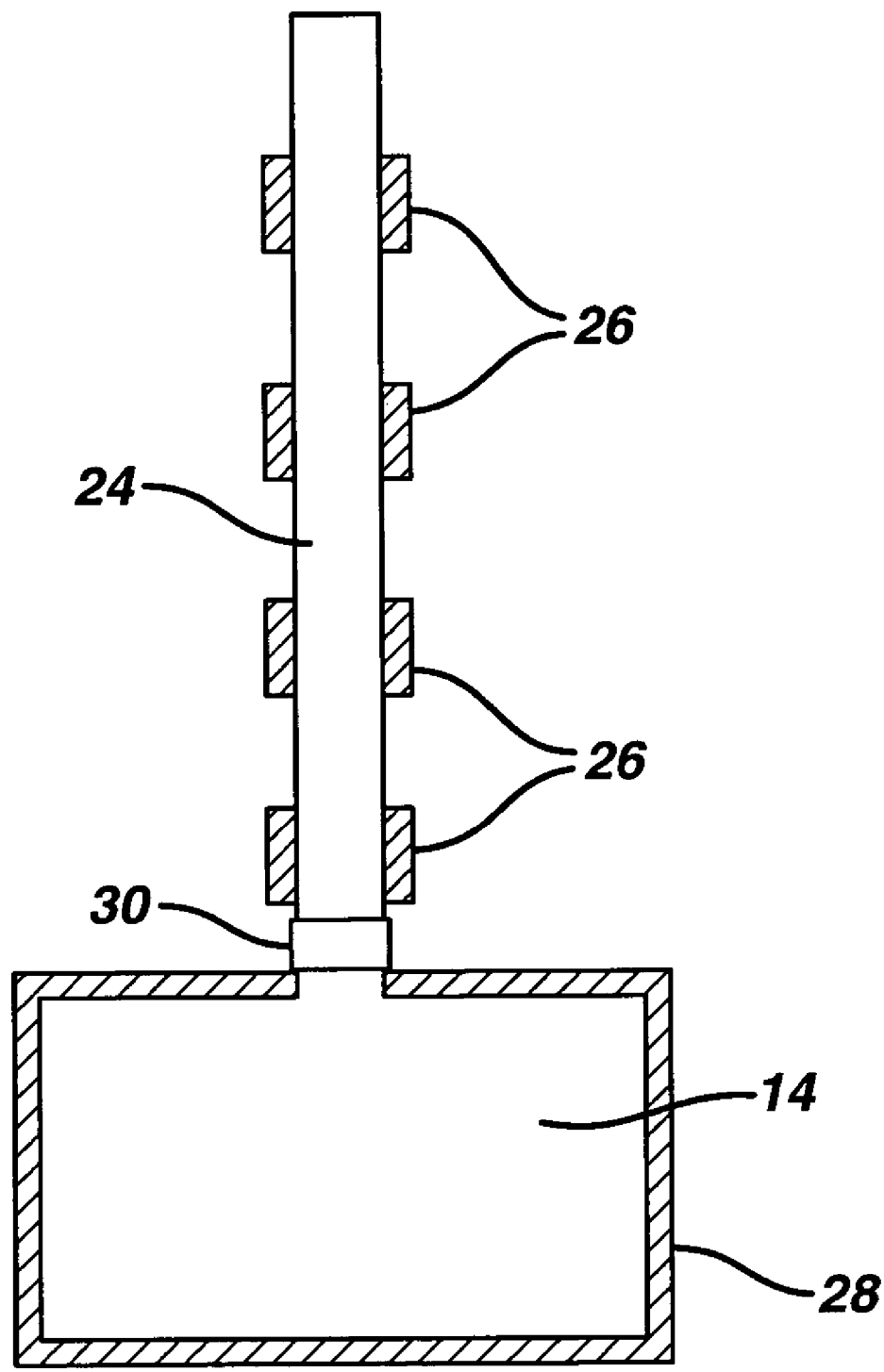
FIG. 2 is a block diagram of a vaporizer and diffusion path of the sterilization system of FIG. 1.

FIG. 1 shows in block diagram form a sterilization system 10 comprising a sterilization chamber 12, a vaporizer 14, and a vacuum pump 16. The vacuum pump is capable of drawing a vacuum on the chamber, preferably as low as 0.5 torr. Between the vacuum pump 16 and the chamber 12, is preferably located at throttle valve 18 and optionally an orifice plate 20. The throttle valve 18 preferably also has good shut-off capability. A pressure gauge 22, preferably located adjacent to the throttle valve 18, shows the vacuum in the chamber 12. A vent valve 23 employing a HEPA antimicrobial filter allows clean sterile air to enter the chamber 12. The vaporizer 14 connects to the chamber 12 by means of an elongated diffusion path 24. Turning also to FIG. 2, the diffusion path 24 incorporates temperature control elements 26 to control the temperature along the diffusion path 24.

Vaporizers suitable for vaporizing a liquid sterilant such as hydrogen peroxide solution are known in the art. Kohler et al. U.S. Pat. No. 6,106,772 and Nguyen et al. U.S. patent application Ser. No. 09/728,973 filed Dec. 10, 2000, both incorporated herein by reference, illustrate vaporizers suitable for the present application. In its simplest for the vaporizer can comprise a small chamber into which the liquid hydrogen peroxide solution is injected. The low pressure in the vaporizer caused by the vacuum in the chamber causes the hydrogen peroxide solution to vaporize.

Preferably, the vaporizer 14 itself incorporates heating elements 28 which control the temperature in the vaporizer to optimize the vaporization process. Preferably, where the vaporizer 14 connects to the diffusion path 24 some form of thermal insulation 30 provided at the interface so that the high temperatures of the vaporizer 14 will not unduly affect the temperature in the diffusion path 24. The vaporizer 14 and diffusion path 24 are preferably formed of aluminum; the thermal insulation 30 can take the form of a polyvinyl chloride (PVC) joint connecting the two together.

The heating elements 28 preferably comprise electric resistance heaters although other types of heating can be employed such as induction heaters, Peltier effect heaters, chemical heaters, fuel based heaters such as natural gas burners, etc.

Further, it is preferable to include a heater 32 inside the chamber 12, preferably near a lower portion of the chamber 12 for revaporizing condensed hydrogen peroxide inside the chamber 12.

The chamber 12 preferably includes a mechanism (not shown) to create a plasma therein. Such mechanism can include a source of radio or low frequency energy as described by Jacobs et al. U.S. Pat. No. 4,643,867, or by Platt, Jr. et al. in published U.S. Application Document No. 20020068012, both of which are incorporated herein by reference.

The present invention achieves its beneficial effect by allowing some of the hydrogen peroxide which is vaporized out of solution in the vaporizer 14 to condense onto the diffusion path 24. After most of the hydrogen peroxide solution has vaporized, the temperature control elements 26 raise the temperature of the diffusion path to allow the condensed hydrogen peroxide to re-vaporize. Water has a higher vapor pressure than hydrogen peroxide, thus hydrogen peroxide in the vapor condenses more easily than water. Thus, the material which condenses in the diffusion path will have a higher concentration of hydrogen peroxide than the starting concentration of the hydrogen peroxide solution in the vaporizer 14.

The temperature control elements 26 in simple form can comprise mere electric resistance heaters. In such case, the low ambient temperature of the diffusion path 24 provides the low temperature for condensing hydrogen peroxide thereon, and the control elements 26 later heat the diffusion path 24 to re-vaporize the now more highly concentrated hydrogen peroxide from the diffusion path 24. Because the vapor pressure of hydrogen peroxide drops with lower temperatures, lower initial temperatures in the diffusion path 24 allows a lower pressure in the chamber 24 without subsequently preventing the condensation of hydrogen peroxide in the diffusion path. Lower chamber pressures promote system efficiency and thus, the temperature control elements 26 can further comprise a chilling component to lower the temperature of the diffusion path below ambient. Suitable chilling components include thermoelectric coolers or a typical mechanical refrigeration system. In such case, the diffusion path 24 would be first chilled, preferably to about 10° C., and then some time after vaporization has begun or even after it has completed, the diffusion path 24 is then heated, preferably up to 50° C. or 110° C.

When vertically oriented as in FIG. 2, the diffusion path 24 can potentially cause the vaporizing sterilant to condense in cooler regions between the temperature control elements 26 and then re-vaporize as it passes the temperature control element 26.

The following example illustrates the benefits of controlling the heat in the diffusion path.

EXAMPLE 1

The efficacy tests were conducted by placing a CSR-wrapped tray (3.5"×12"×20") consisting of representative medical devices and test lumens in a 20-liter aluminum chamber (4.4"×12"×22") A one-inch stainless steel wire inoculated with at least $1\times10^6$ Bacillus stearothermophilus spores was placed in the center of each of the test lumens. The effects with and without temperature control of the diffusion path were investigated with both a TEFLON, poly(tetrafluoroethylene)lumen having an internal diameter of 1 mm and a length of 700 mm, and a stainless steel lumen having an internal diameter of 1 mm, and a length of 500 mm. All lumens were open at both ends. Each of the samples was subjected to a sterilization cycle in a 20 liter vacuum chamber, which was held at 40° C. and 3 torr for 5 minutes. 1.44 ml of a 59% solution of hydrogen peroxide in water was injected at atmospheric pressure into the vaporizer which was held at 60° C. The 5 minute clock then started and the chamber was pumped down to 3 torr, which took less than one minute. In one case the diffusion path 24 had an initial temperature of 30° C. for the first minute while the chamber was evacuated to 3 torr and was then heated to 50° C. to release the condensed peroxide from the diffusion path into the chamber for the remainder of the cycle while pressure was maintained at 3 torr. In the other case, the diffusion path was held at 50° C. throughout the cycle. By maintaining the diffusion path at 50° C., no or little peroxide was retained in the diffusion path. Sterilization effectiveness was measured by incubating the test samples in growth media at 55° C. and checking for growth of the test organism. Table 1 shows the results of these tests.

TABLE 1

| Lumen Type | ID & Length | 50° C. Diffusion Path Throughout Process | 30° C. Diffusion Path For One Minute Then increased to 50° C. |
| --- | --- | --- | --- |
| Teflon | 1 × 700 | 2/2 | 0/3 |
| Stainless Steel | 1 × 500 | 1/2 | 0/3 |

When the diffusion path temperature was maintained at high temperature throughout the process, all of the samples in the TEFLON lumen tested positive for bacteria growth, indicating failure of sterilization, and one of two samples in the stainless steel lumen tested positive. Under the same conditions, but with an initially lower temperature diffusion path which was heated starting one minute after the diffusion began, none of the samples tested positive. Condensing the peroxide in the diffusion path during the initial vaporization stage and then re-vaporizing the condensed peroxide from the diffusion path into the chamber greatly enhance the efficacy.

Additional efficiencies can be achieved by alternating cool and warm regions in the diffusion path 24 as primarily illustrated in FIG. 2. The temperature control elements 26, in simple form heating elements, are spaced apart from one another. Also, preferably, the diffusion path 24 is vertical in this respect. As the hydrogen peroxide solution vaporizes and passes through the diffusion path 24, it is thought that it may alternately condense and re-vaporize as it passes over the heated and unheated sections of the diffusion path 24. The diffusion path could alternatively comprise alternating heating and cooling elements.

The heater 32 within the chamber 12 acts similarly to the heating of the diffusion path 24. By controlling the heater 32 temperature, the peroxide can be first condensed on the heater 32 and then re-vaporized into the chamber 12 to concentrate the peroxide.

A preferred cycle would be a modification of a cycle described in the Wu et al. U.S. Pat. No. 6,365,102, incorporated herein by reference. A series of pre-plasma energy additions with venting in-between dries moisture from the chamber 12. A vacuum is then drawn upon the chamber 12 and the hydrogen peroxide solution injected into the vaporizer 14. Alternatively, the peroxide solution can also be injected at atmospheric pressure. Some of the vaporizing solution condenses upon the cool diffusion path 24. After a time sufficient for most or all of the hydrogen peroxide solution to vaporize from the vaporizer 14, the diffusion path 24 is warmed by the temperature control elements 26 and the condensed hydrogen peroxide solution re-vaporizes. At about this time, the throttle valve 18 is closed and the pump 16 turned off to seal the chamber 12. Much of the water fraction of the hydrogen peroxide solution has thus been drawn out of the chamber 12 by the vacuum pump 16 and the remaining hydrogen peroxide solution which re-vaporizes from the diffusion path 24, or from the heater 32 in the chamber 12 if present, is of a higher hydrogen peroxide concentration than the starting solution. Preferably, a computer based control system (not shown) controls the functions of the process for ease and repeatability.

The hydrogen peroxide vapor thus produced contacts an article 34 or articles 34 in the chamber 12 and effects sterilization thereof. If those articles 34 have diffusion restricted areas, such as long, narrow lumens, it may be preferable to then vent the chamber 12 and allow clean sterile air therein to drive the hydrogen peroxide vapor deeper into the diffusion restricted areas. Then the chamber 12 is again subjected to vacuum and an additional injection of hydrogen peroxide, preferably with the heating sequence on the diffusion path, is repeated. After a time period sufficient to effect sterilization of the article 34, preferably with a six-log reduction in challenge organisms such as *Bacillus stearothermophilus*, a plasma is lit within the chamber 12, thereby enhancing the sterilization and breaking down the hydrogen peroxide into water and oxygen.

The orifice plate 20 can enhance the effect of concentrating the hydrogen peroxide during its vaporization. As described in the Lin et al. U.S. Pat. No. 5,851,485, incorporated herein by reference, a controlled or slow pump-down of the chamber 12 initially draws off more water than hydrogen peroxide from solution as the water has a higher vapor pressure, thereby leaving a higher concentration hydrogen peroxide behind. Controlling the pump-down can be difficult as vacuum pumps generally do not throttle back well and throttle valves in such service are difficult to control and expensive. By placing the orifice plate 20 in the flow path to the pump 16, the amount of atmosphere from the chamber 12 exhausted by the pump 16 is limited, and by selecting a proper size orifice 36 in the plate 20 can be controlled to a rate which effectively concentrates hydrogen peroxide in the chamber 12.

Turning also to FIG. 3, a system 10a, similar in most respects to the system 10 of FIGS. 1 and 2, with like part numbers denoted with an "a" appended thereto, also incorporates an orifice plate 20a. However, to allow a quick pump-down of the chamber 12a, yet retain the controlled pump-down benefits of the orifice plate 20a, it incorporates two path ways from the pump 16a to the chamber 12a. A first pathway 40 contains a throttle valve 42 and a second pathway 44 contains a throttle valve 46 and the orifice plate 20a. Thus, during initial pump-down the first throttle valve 42 is open leaving the pump 16a freely connected to the chamber 12a. As the chamber 12a approaches the vapor pressure of water, the first throttle valve 42 is closed thereby forcing the pump 16a to evacuate through the orifice plate 20a and thus draw out of the chamber 12a at a slower, controlled rate more conducive to preferentially drawing water out of the hydrogen peroxide solution and out of the chamber 12a.

Turning also to FIGS. 3A and 3B, a system 110 similar to that of FIG. 1 is shown. Here, rather than use two paths as in the system 10a of FIG. 3, a valve 112 comprises a valve body 114, a valve seat 116 and a valve element 118, such as a butterfly disc, plug or the like. An orifice 120 is provided through the valve element. Thus, when the valve 112 is open evacuation can occur quickly, and when the valve 112 is closed it can occur more slowly. Such a valve could also be employed between the vaporizer 14 and the chamber 12 to further control the preferential vaporization and removal of the water from the germicide solution.

Figure 4:
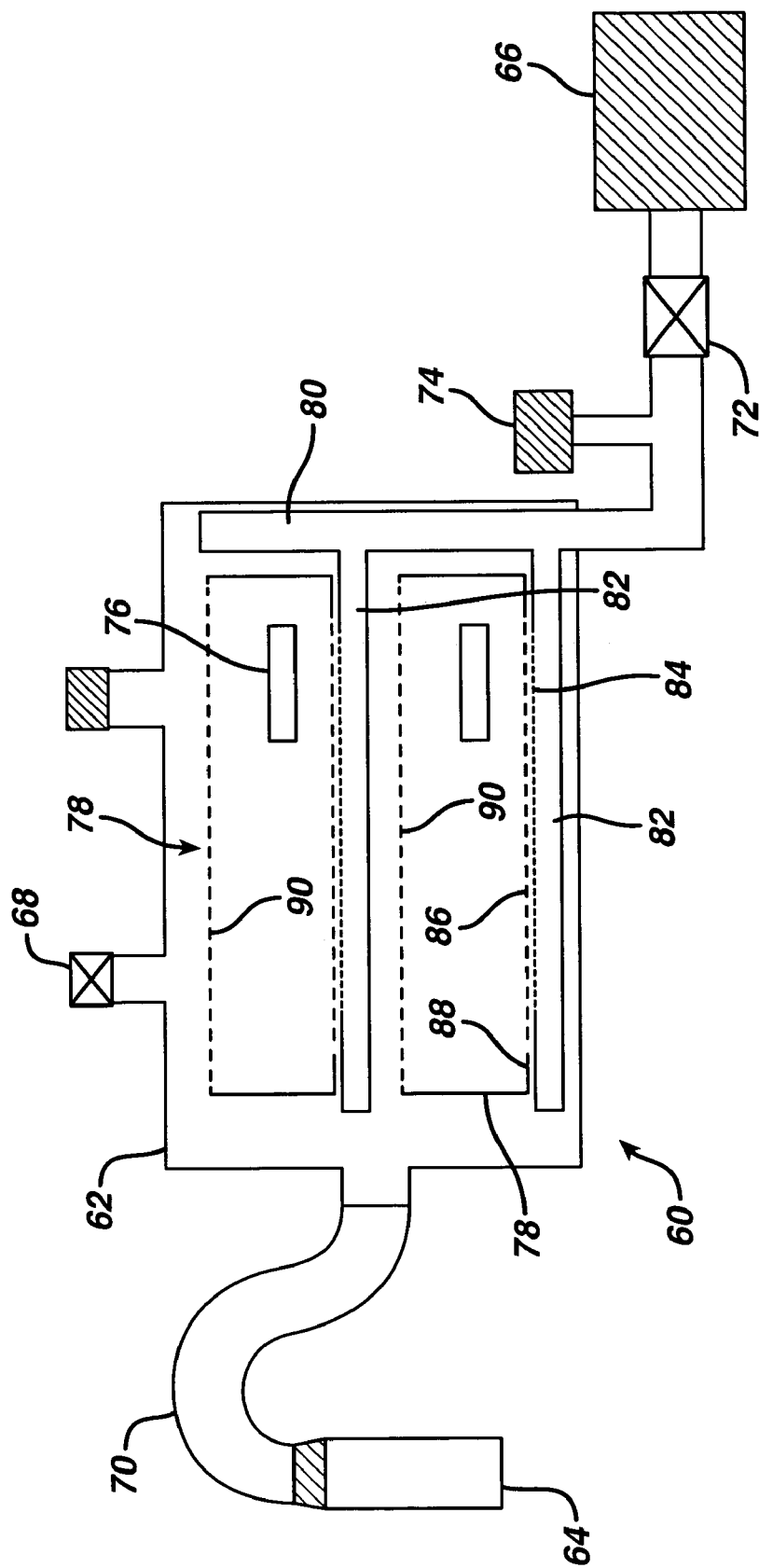
FIG. 4 is a block diagram of an alternate embodiment of a sterilization system according to the present invention.

Turning now to FIG. 4, while highly concentration of the sterilizing vapor is helpful in achieving sterilization efficiency and efficacy, getting the vapor into contact with the items to be sterilized is also a concern. Typically, the low pressures (0.5 torr to 10.0 torr) inside of a chamber 12 promotes quick diffusion of the sterilant vapor to all areas therein.

FIG. 4 illustrates a sterilization system 60 comprising a chamber 62 having a vaporizer 64, vacuum pump 66 and vent 68 connected thereto. Preferably, an elongated, temperature controlled diffusion path 70 as previously described connects the vaporizer 64 to the chamber 62. A throttle valve 72 and pressure gauge 74 are provided at the pump 66.

Articles 76 to be sterilized are placed into trays or containers 78. Two types of packaging are commonly used in preparing articles 76 for sterilization. In one, the articles 76 are placed into a tray having a plurality of openings therein, and the tray is then wrapped with a material such as CSR wrap which passes sterilizing gases and blocks contaminating microorganisms. Such a tray is described in the Wu, U.S. Pat. No. 6,379,631, incorporated herein by reference. An alternative package comprises a sealable container with several ports, preferably on top and bottom surfaces thereof, with each of the ports covered by a semi-permeable membrane which passes sterilizing gases and blocks admission of contaminating microorganisms. Such a container is described in Nichols U.S. Pat. No. 4,704,254, incorporated herein by reference. The first type of packaging is typically called a "tray" and the second a "container." However, the term "container" as used herein is meant to refer to any container, packaging or enclosure suitable for containing articles to be sterilized in a chemical vapor environment.

The pump 66 connects to the chamber 62 via an exhaust manifold 80. The manifold 80 comprises one or more shelves 82 for supporting and receiving one or more containers 78 and which connect fluidly through the throttle valve 72 to the pump 66. An opening, or preferably a plurality of openings 84 on the upper surfaces of the shelves 82 allow the pump 66 to draw atmosphere within the chamber 62 through the openings 84, through the manifold 80 and out through the pump 66.

The containers 78 preferably have openings 86 on a lower surface 88 thereon and additional openings 90 on at least one other surface. When the containers 78 are placed on the shelves 82 atmosphere being exhausted by the pump 66 is drawn in part through the openings 90 into the container 78, through the container into contact with the article or articles 76 therein and then out through the openings 86 into the manifold 80 through the openings 84 therein. When the atmosphere being so exhausted contains a sterilizing gas it enhances its penetration into the containers 78 and into contact with the articles 76 therein.

Sterilizing gases are so exhausted during the previously described cycle as the sterilant solution is vaporizing and immediately before the second admission of hydrogen peroxide. Such a cycle can also further provide a pump-down after some period of diffusion. After admitting the sterilant vapor the chamber 62 pressure rises slightly due to the presence of additional gas therein, typically from about 0.5 torr to about 10 torr. Higher pressures are as efficient with higher load and chamber temperatures.

Figure 5:
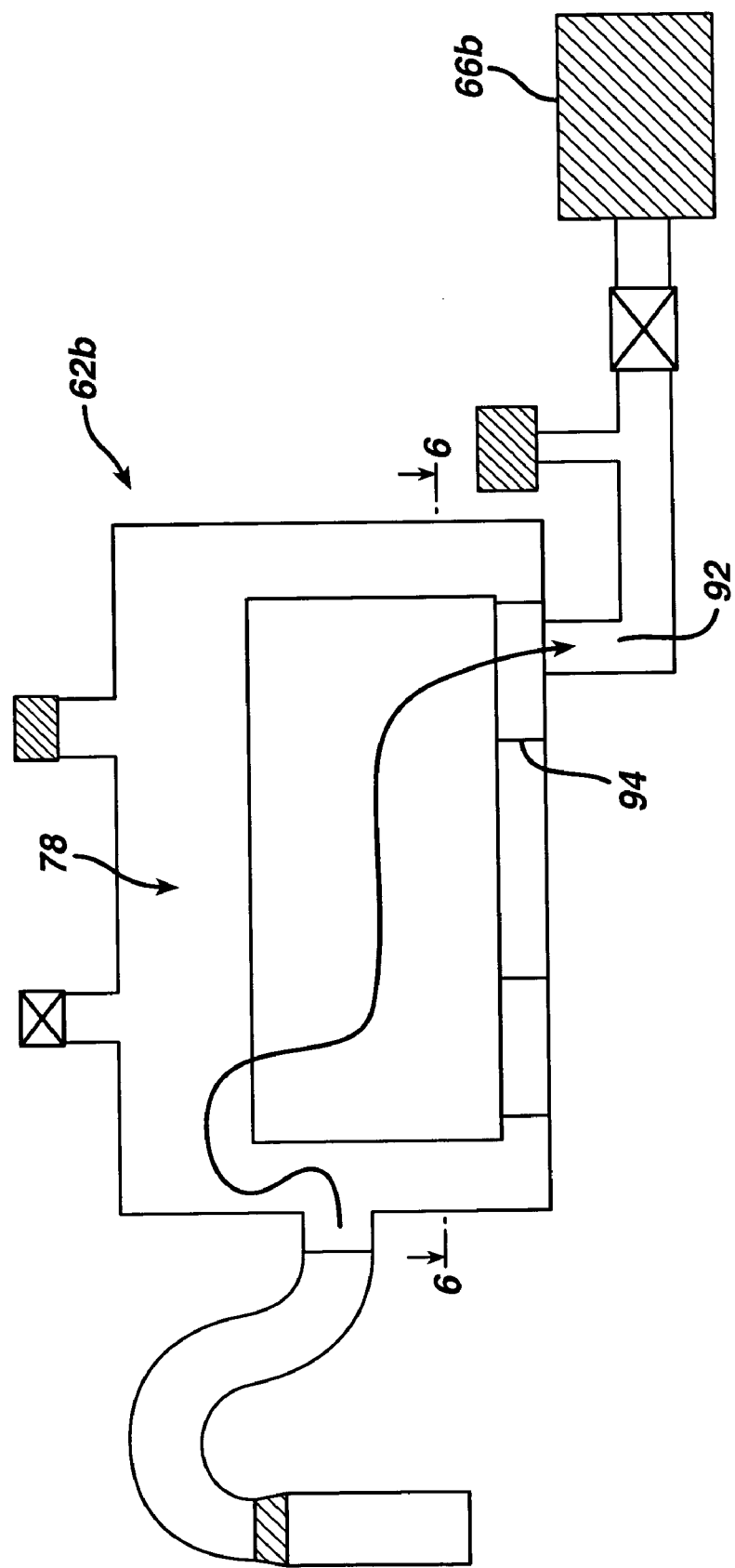
FIG. 5 is a block diagram of an alternate embodiment of a sterilization system according to the present invention.
Figure 6:
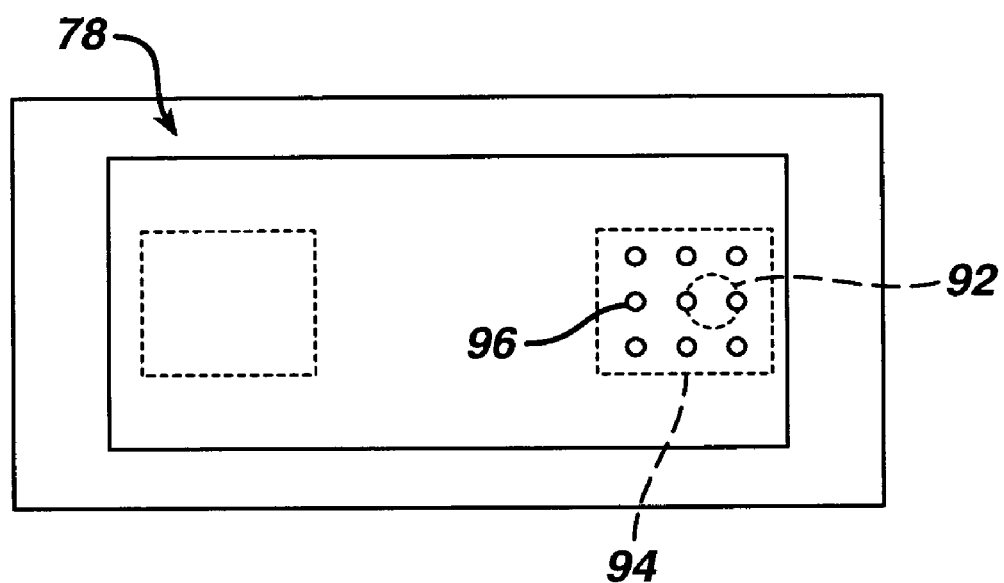
FIG. 6 is a section view taken along lines 6-6 of FIG. 5.

Turning also to FIGS. 5 and 6, an alternative design (in which like part numbers to those of the design of FIG. 4 are designated with a "b" appended thereto) replaces the manifold 80 of the design of FIG. 4 with a simple port 92. The port 92 is covered by a support 94 for the container 78, the support 94 having a plurality of openings 96 therethrough so that the chamber 62b is in fluid communication with the pump 66b through the container 78, the support 94 and the port 92. The support 94 can be removable.

Figure 7:
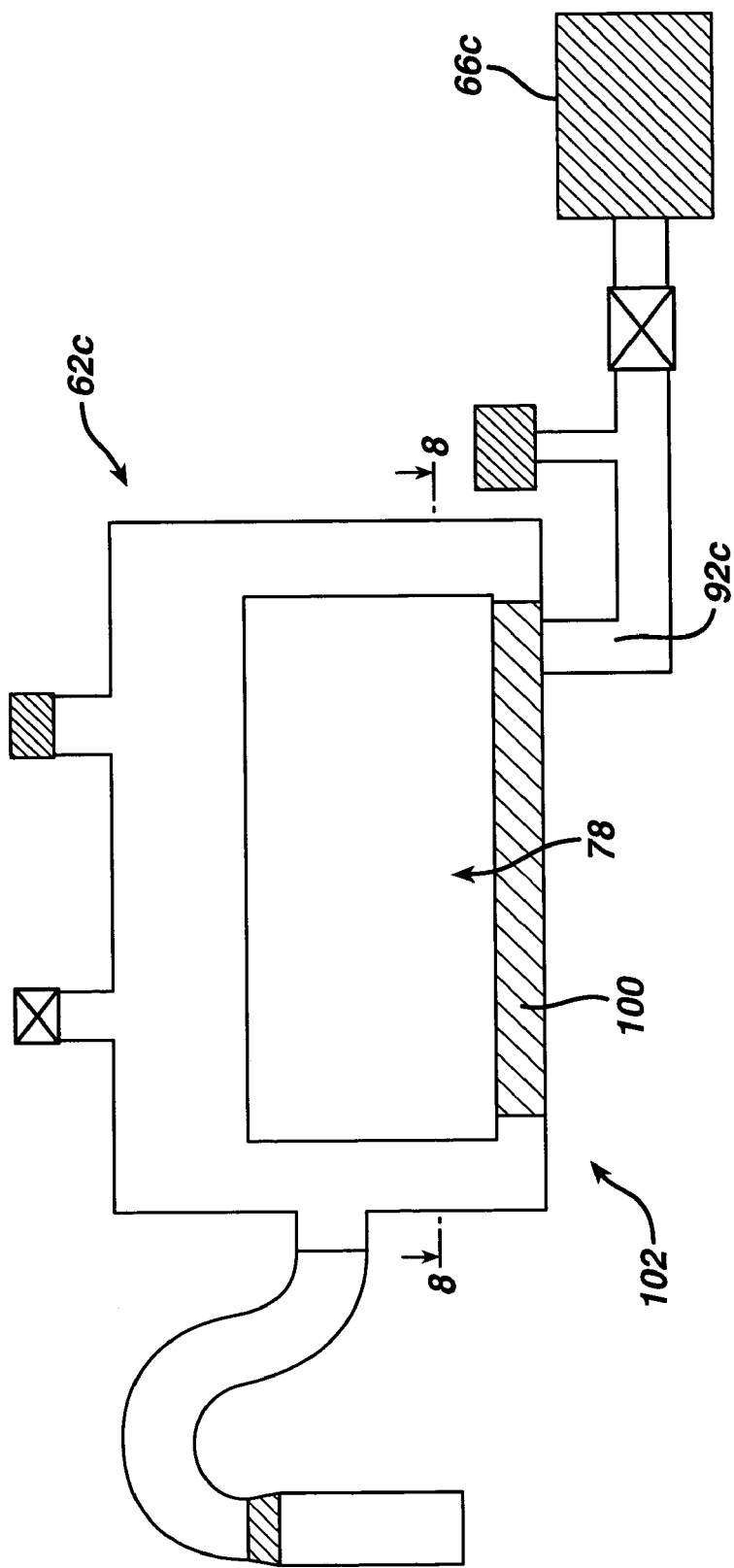
FIG. 7 is a block diagram of an alternate embodiment of a sterilization system according to the present invention.
Figure 8:
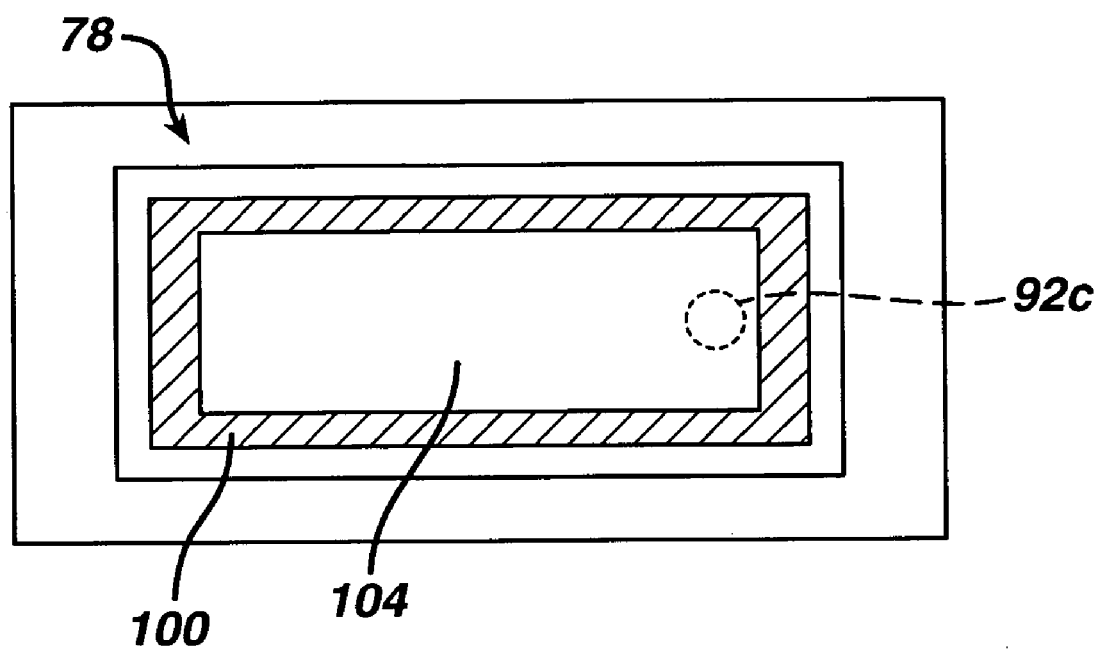
FIG. 8 is a section view taken along lines 8-8 of FIG. 7.

Turning also to FIGS. 7 and 8 (in which like part numbers to those of the designs of FIGS. 4 to 6 are designated with a "c" appended thereto) shows a support 100 resting on a surface 102 in the chamber 62c through which penetrates the port 92c. The support 100 surrounds the port 92c. Thus, most or all of the atmosphere being exhausted by the pump 66c passes through the container 78 into a space 104 formed between the container 78, the support 100 and the surface 102 and then onto the pump 66c through the port 92c.

Figure 9:
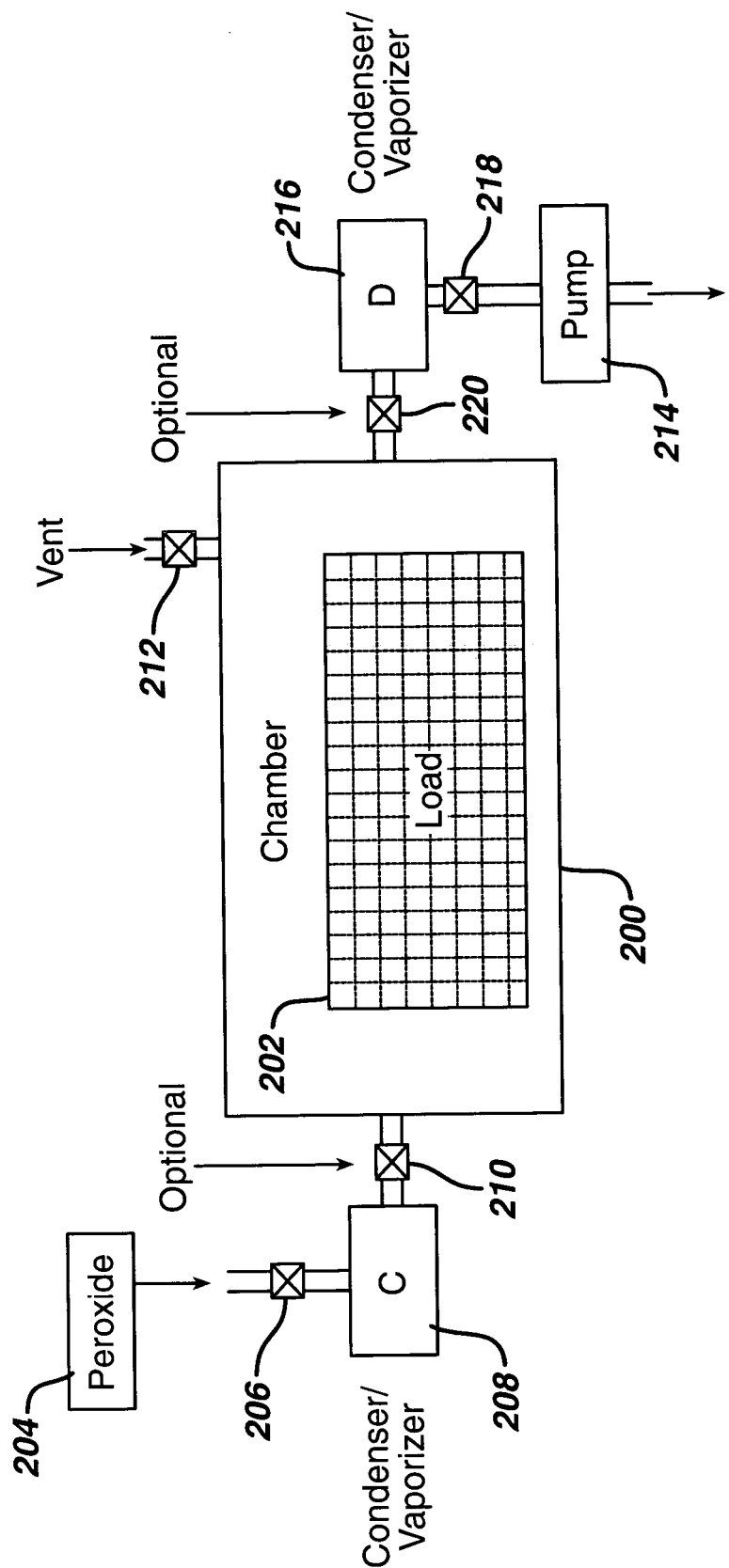
FIG. 9 is a block diagram of a sterilization system according to the present invention.

FIG. 9 discloses an alternative system in which, similar to the system of FIG. 1, a portion of the vaporized germicide solution can be condensed and the solvent, typically water, which has not condensed as quickly is removed from the atmosphere to further concentrate the germicide. The germicide is then revaporized to produce a more concentrated germicidal vapor for more efficient sterilization. The system comprises a sterilization chamber 200 containing a load 202 of items to be sterilized. A source 204 of liquid germicide solution provides the solution through a valve 206 to a first vaporizer/condenser 208 where it is vaporized and then supplied to the chamber 200. A valve 210 can be provided to isolate the vaporizer/condenser 208 from the chamber 200. The chamber 200 is also provided with a valved vent 212.

A vacuum pump 214 provides for lowering the chamber pressure as described in reference to the previous embodiments. Between the pump 214 and the chamber 200 a second vaporizer/condenser 216 is provided for condensing the vaporized solution. Preferably valves 218 and 220 isolate the second vaporizer/condenser 216 from the pump 214 and chamber 200 respectively.

Figure 10:
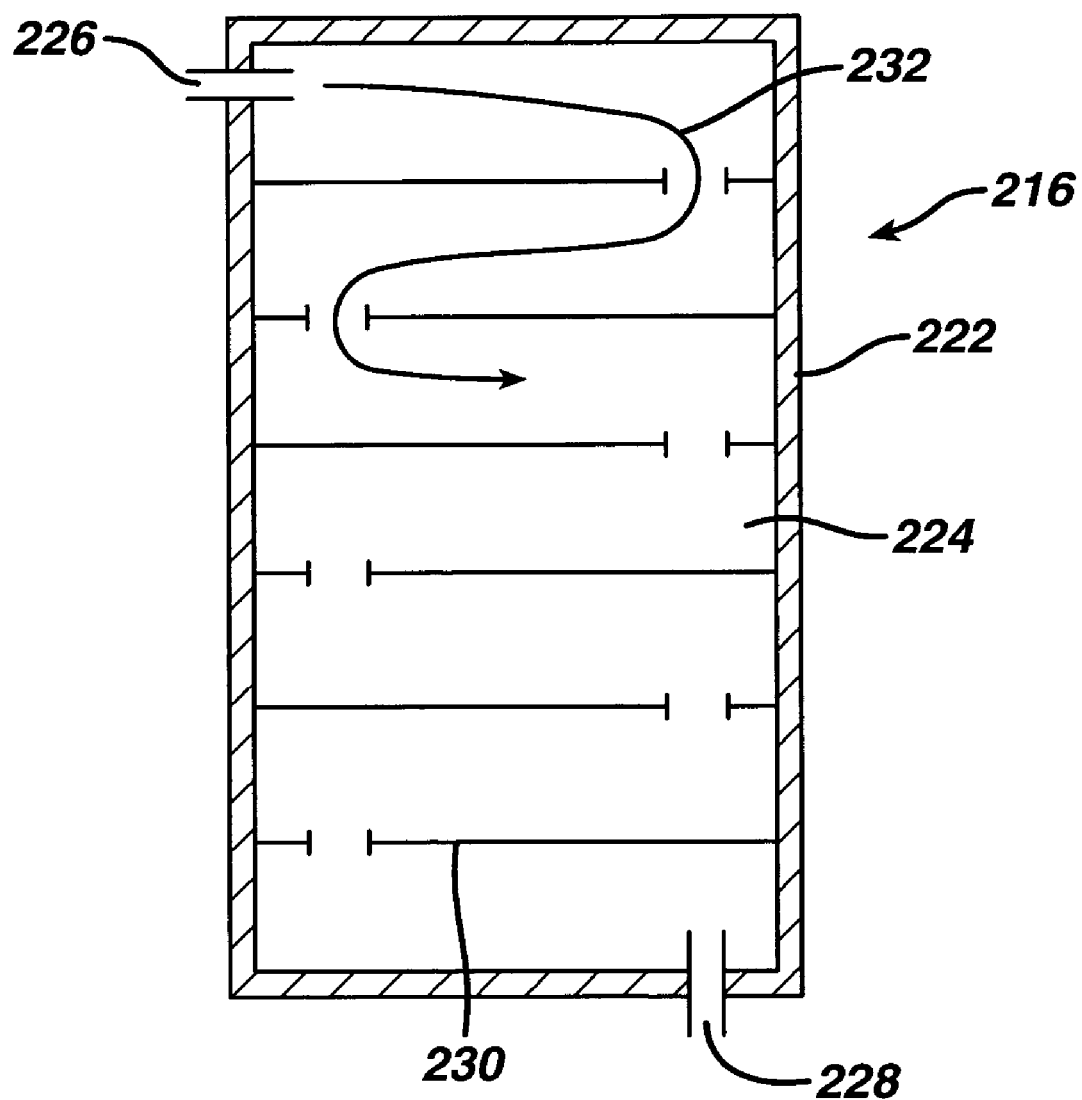
FIG. 10 is a cut-away view of an outlet condenser/vaporizer for use in the system of FIG. 9.

Turning also to FIG. 10 a simple version of the second vaporizer/condenser 216 preferably comprises walls 222 defining an enclosure 224 having an inlet 226 connected to the chamber 200 and an outlet 228 connected to the pump 214. A plurality of baffles 230 provides a torturous flow path 232 through the vaporizer/condenser 216. The walls 222, and potentially the baffles 230, are temperature controllable to enhance condensation of and re-vaporazation of the solution.

Figure 11:
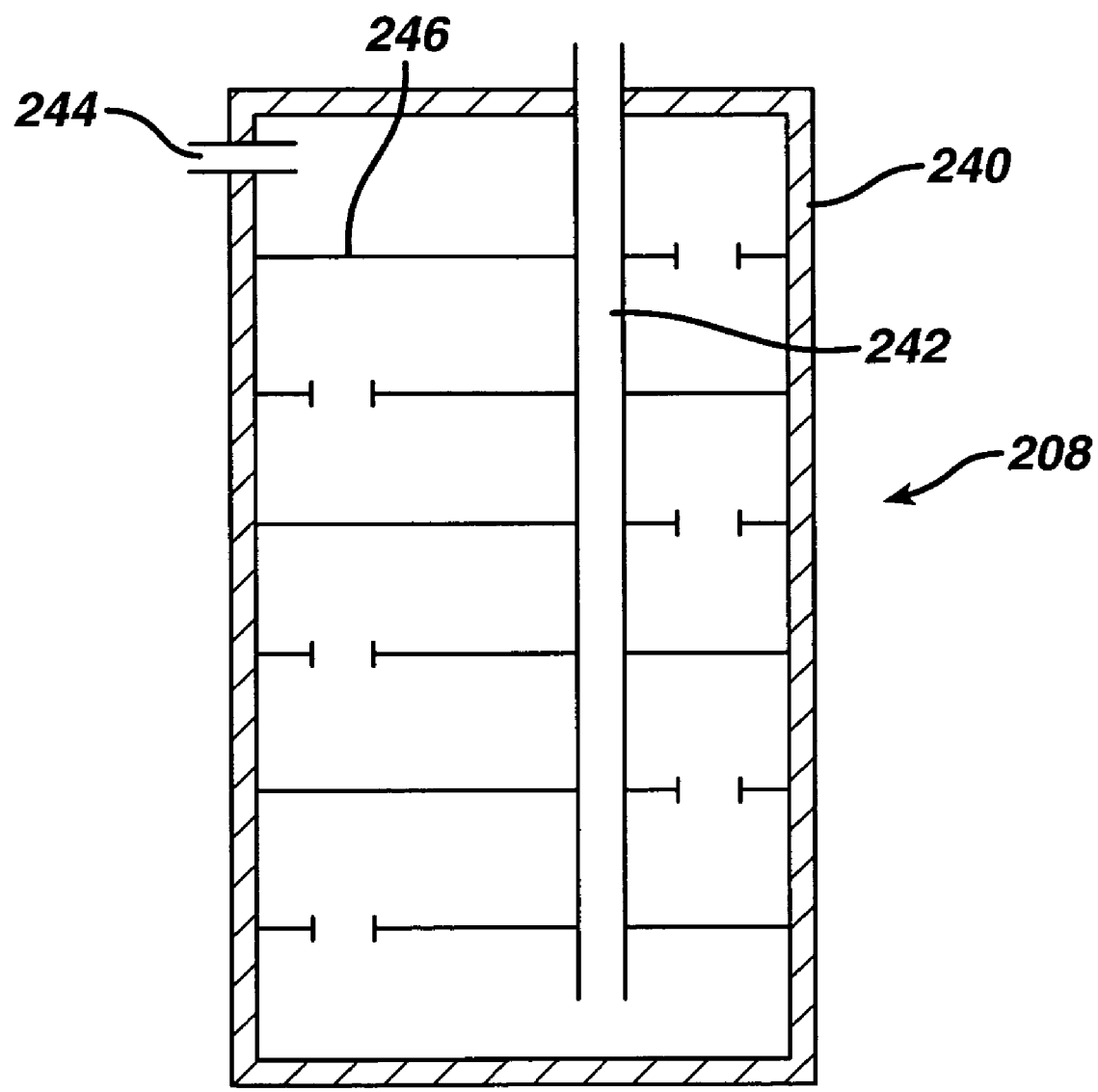
FIG. 11 is a cut-away view of an inlet condenser/vaporizer for use in the system of FIG. 9.
Figure 12:
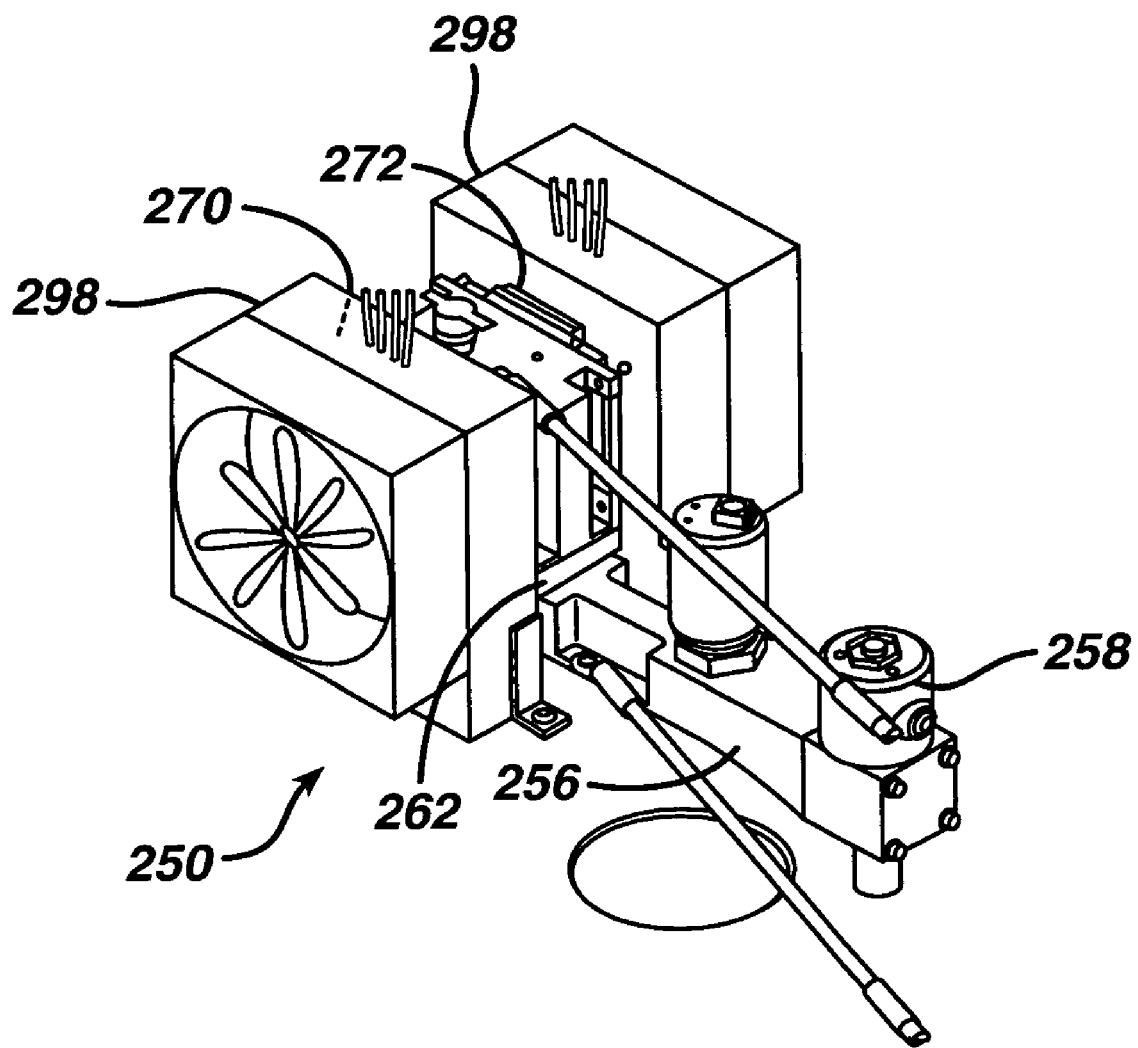
FIG. 12 is a perspective view of an alternative inlet condenser/vaporizer for use in the system of FIG. 9.
Figure 13:
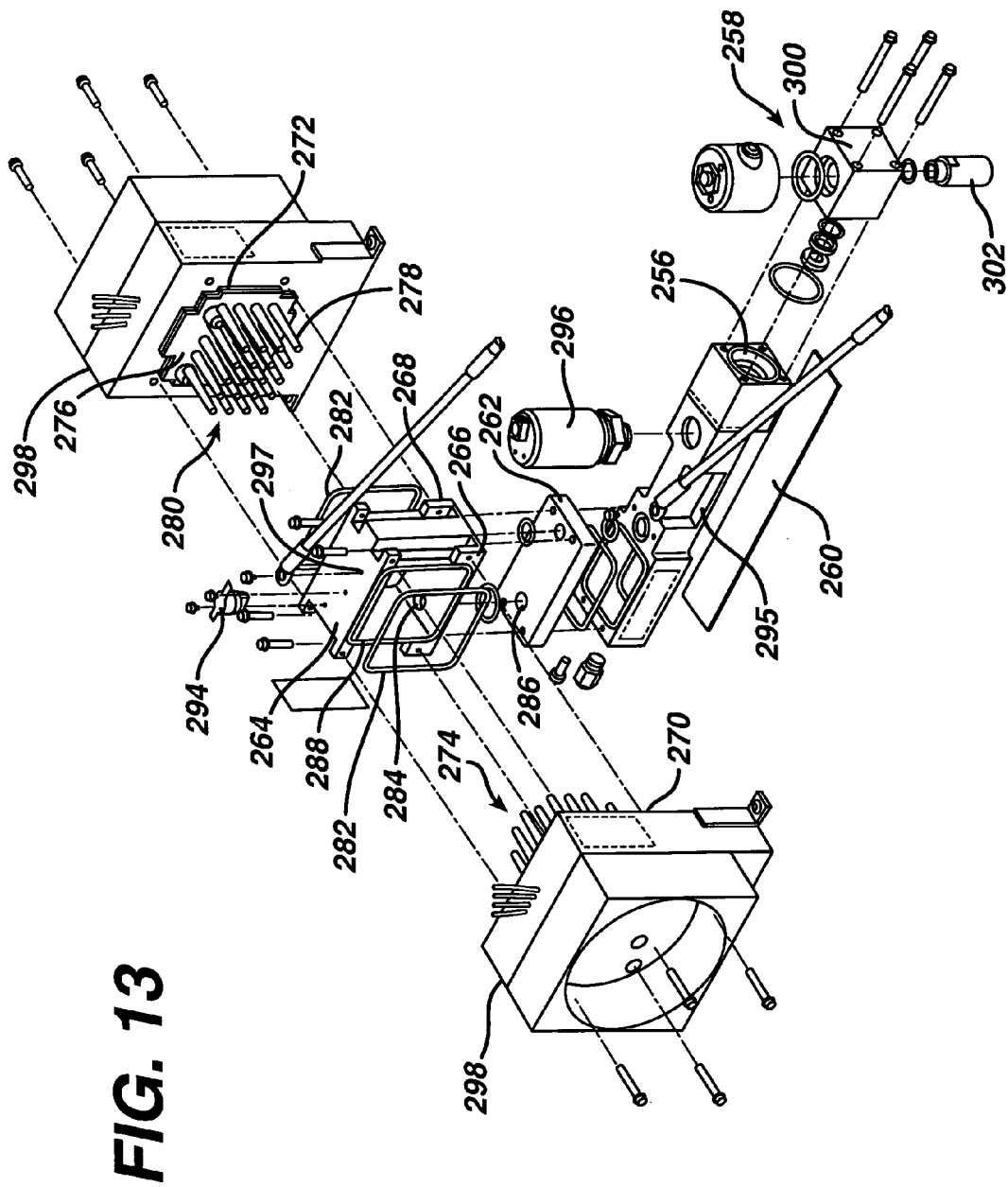
FIG. 13 is an exploded perspective view of the condenser/vaporizer of FIG. 12.
Figure 14:
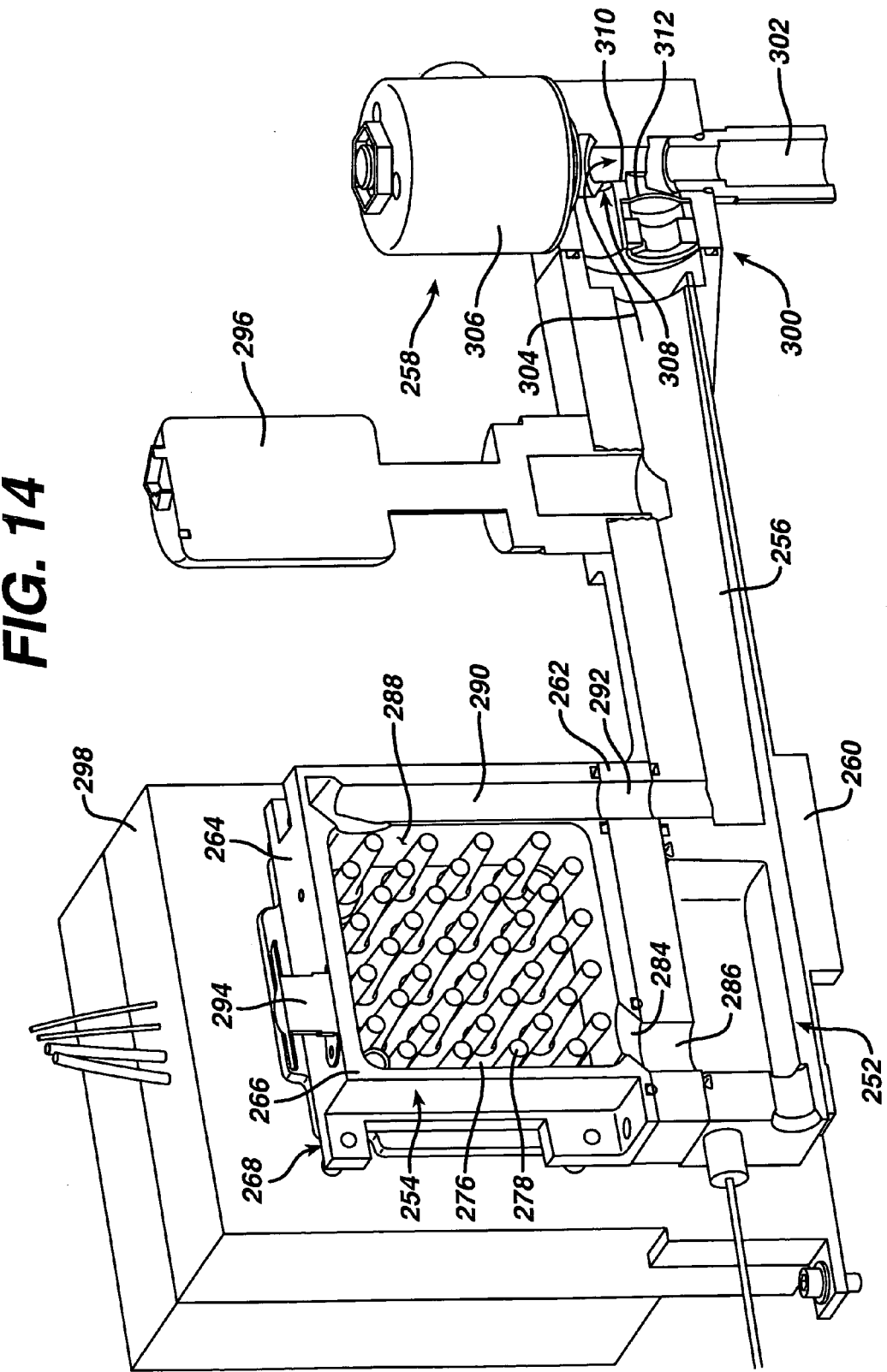
FIG. 14 is a section view taken along lines 14-14 of FIG. 12.
Figure 15:
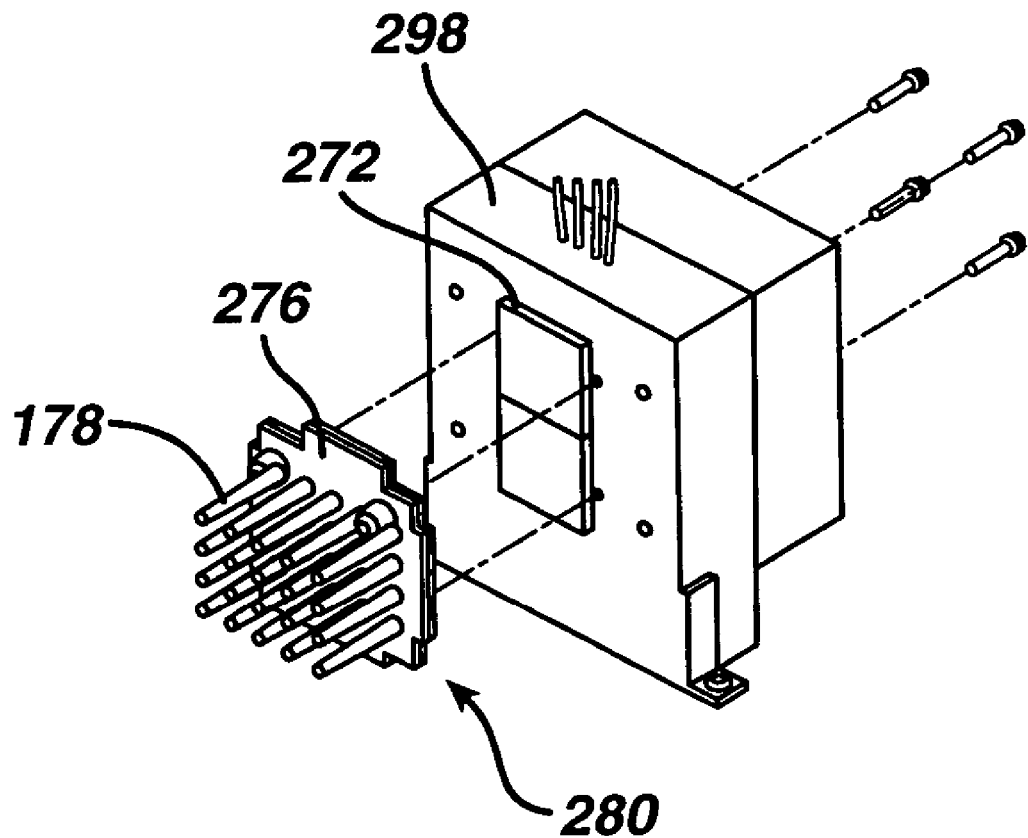
FIG. 15 is an exploded perspective view of a thermoelectric heat pump and rod assembly employed in the condenser/vaporizer of FIG. 12.

A similar structure with an inlet can be employed on the first vaporizer/condenser 208 as well. Turning also to FIG. 11, a simple version of the first condenser/vaporizer 208 is illustrated. It comprises an enclosure 240 having an inlet 242 connected to the source of solution 204 (not shown in FIG. 11) and an outlet 244 connected to the chamber 200 (not shown in FIG. 11). A plurality of baffles 246 provides a tortuous flow path through the first vaporizer/condenser 208. The enclosure 240 and potentially the baffles 246 are temperature controllable to enhance condensation and revaporization of the solution.

In a simple cycle, a liquid germicide solution, such as hydrogen peroxide and water is admitted into the first vaporizer/condenser 208 where it is vaporized and then flows into the chamber 200 which is at a low pressure, all as described in reference to previous embodiments herein. During vaporization and for sometime thereafter pump 214 continues to exhaust atmosphere from the chamber 200. By controlling temperature and pressure this preferentially vaporizes water from the solution over the hydrogen peroxide and the water vapor is extracted from the system via the pump 214 to concentrate the hydrogen peroxide solution during the vaporization phase. Additionally, hydrogen peroxide, having the lower vapor pressure, will tend to condense more quickly than the water vapor in the first vaporizer/condenser 208. As the pump 214 continues to exhaust atmosphere from the chamber 200 the vaporized hydrogen peroxide solution flows out of the chamber and into the second vaporizer/condenser 216 where a portion thereof will condense. Due to the preferential condensation of hydrogen peroxide over the water more of the water vapor will pass through the condenser 216 uncondensed and be exhausted via the pump 214 thus allowing further concentration of the hydrogen peroxide solution. At some point, the pump is turned off and the valve 218 closed. The condensed hydrogen peroxide within the vaporizer/condenser 216 is then re-vaporized preferably by heating the condenser 216. This hydrogen peroxide will have a higher concentration for more efficient sterilization of the load 202.

Turning also to FIGS. 12 through 15, a more elaborate condenser/vaporizer 250 is illustrated. In gross, it comprises an inlet manifold 252 which connects to the source of sterilant solution 204 and which acts as a vaporizer to provide initial vaporization, a condensing/revaporization section 254, an outlet manifold 256 and a control valve 258 via which the vaporizer/condenser 250 connects to the chamber 200. A resistance heater 260 affixes to the inlet manifold 252 and to the outlet manifold 256 to provide heat to assist in the initial vaporization within the inlet manifold 252 and to prevent condensation in the outlet manifold 256. Other types of heating can be employed such as induction heaters, Peltier effect heaters, chemical heaters, fuel based heaters such as natural gas burners, etc.

Preferably, the inlet manifold 252 and outlet manifold 256 are formed of aluminum. Further, an insulator 262 is provided between the inlet manifold 252 and the vaporizer/revaporizer section 254.

The condensing/revaporization section 254 comprises a housing 264, preferably formed of aluminum, open on a first side 266 and second side 268. A first thermo-electric device 270 and second thermo-electric device 272 affix to the first side 266 and second side 268, respectively. The thermoelectric devices 270 and 272 preferably operate under the Peltier effect, although other classes of thermoelectric devices could be substituted therefor. More conventional heat pumps, such as freon or ammonia based systems can also be employed with somewhat greater complexity.

A first rod assembly 274, comprising a plate 276 and a plurality of rods 278 extending normally therefrom affixes to the first thermo-electric device 270 with the rods 278 extending laterally into the housing 264. A second rod assembly 280 similarly attaches to the second thermo-electric device 272 with its rods 278 extending laterally into the housing 264 in facing relationship to the first rod assembly 274. The rod assemblies 274 and 280 are preferably formed of aluminum.

Preferably, the rods 278 extend almost to, without touching, the opposing plate 276. Also, the rods 278 from the two rod assemblies 274 and 280 lie in a generally parallel relationship with each other with a spacing therebetween designed to, along with the volume within the vaporizer/revaporizer section 254, provide a preferred flow rate of the vaporized sterliant therethrough to provide efficient condensation on to the rods 278. Preferably, a flow rate is in the range of 0.1 ft/sec to 5 ft/sec, and more preferably a flow rate of 0.24 ft/sec is provided.

In a small condenser with a vapor path length of 3 inches, the residence time would be 1 second at a preferred velocity of 0.24 ft/sec. This residence time would be sufficient for the vaporized sterilant to interact with the cooler condenser surfaces and to condense. For a typical injection volume of 2 ml of sterilant solution, the surface area of the condensing/revaporization section 254 would be about 90 square inches to permit mass transfer for condensation. High temperature at low pressure in the initial vaporizer (inlet manifold 252) maintains the water and hydrogen peroxide in the vapor phase for delivery to the condensing/revaporization section 254. For example, a vaporizer temperature of 70 degrees C. or greater at a pressure of 125 torr or lower ensures that a 59 wt % solution of hydrogen peroxide and water will be in the vapor phase.

As vapor enters the condensing/revaporization section 254, which has a lower temperature, the hydrogen peroxide condenses on the cooler surface forming a concentrated solution. The temperature and pressure therein determine the concentration of the condensed solution. For example, at 50 degrees C. and 13 torr in the condensing/revaporization section 254, the condensed hydrogen peroxide concentration would be 94 wt %. At 30 degrees C. and 3.8 torr, the condensed hydrogen peroxide concentration also would be 94 wt %. As the pressure in the condensing/revaporization section 254 is lowered, the temperature must also be lowered to maintain the same concentration of solution.

The orifice 308 offers the advantage of a more concentrated solution by restricting the flow from the condensing/revaporization section 254 to provide a more controlled vaporization. Variations in pressure in the condensing/revaporization section 254 and in the vaporizer due to vacuum pump pressure fluctuations are dampened out by the orifice 308 to prevent surges of water vapor from carrying hydrogen peroxide droplets from the condensing/revaporization section 254. Another advantage of flow restriction by the orifice 308 is achieving a low pressure (less than 1 torr) in the sterilization chamber 200 to improve the diffusion coefficient in lumens while maintaining a greater pressure in the vaporizer/condenser 250 to operate at a greater temperature in the condensing/revaporization section 254. Without an orifice 308, sterilization chamber 200 and vaporizer/condenser 250 pressures must both be reduced to the same low pressure together, and the condenser must be operated at a very low temperature to maintain equilibrium of the solution. A lower condenser temperature is more difficult to control and may produce ice or condensate, which requires a more expensive design to protect electrical equipment.

An O-ring 282 seals the plates 276 on the thermo-electric devices 270 and 272 against the housing 264. An aperture 284 through the housing 264 aligns with an aperture 286 through the insulator 262 to place a chamber 288 defined by the housing 264 into fluid communication with the inlet manifold 252. An outlet passage 290 in the housing 264 connects to an upper portion of the chamber 288 and to a second aperture 292 through the insulator 262 which in turn aligns with the outlet manifold 256 to place the chamber 288 in fluid communication with the outlet manifold 256. A safety thermostat 294 atop the housing 264 is wired outside of the control system to shut down heating of the vaporizer/condenser 250 above a predetermined temperature. Temperature sensors 295 and 297 measure temperature in the inlet manifold 252 and condensing/revaporization section 254 respectively. A pressure sensor 296 interfaces with the outlet manifold 256. Heat sinks 298 having fan housings attach to each of the thermoelectric devices 270 and 272.

The outlet manifold connects to a valve manifold 300 which provides three possible flow paths between the vaporizer/condenser 250 outlet manifold 256 and a valve manifold outlet 302 from the valve manifold 300. The valve manifold outlet 302 communicates with the main chamber 200. A main flow passage 304 is controlled by a valve 306 which can open to allow flow through the main passage 304 to the valve manifold outlet 302 or close to block such flow. The second passage is through an orifice 308 in an orifice plate 310 which provides a flow restriction to enhance the ability to preferentially draw water vapor from the vaporizer/condenser 250. A third potential passage is through a rupture disk 312 which is designed to rupture in case of a catastrophic overpressure within the housing chamber 288, such as in the unlikely event that an oxidizable sterilant such as hydrogen peroxide combusts therein. The orifice 308 could be moved to a position within the shut-off valve 306, similar to that described in reference to the valve element 118 in FIGS. 3A and 3B.

In operation, the main chamber is first evacuated to a low pressure sufficient to induce vaporization, such as 0.4 torr and the valve 306 is closed placing the vaporizer/condenser 250 into fluid communication with the chamber 200 solely through the orifice 308. The inlet manifold 252 is heated with the heater 260 and a quantity of sterilant solution such as a 59% hydrogen peroxide/water solution is injected into the inlet manifold 252 where it vaporizes and diffuses into the housing 264 through the apertures 286 and 284. The thermo-electric devices 270 and 272 at this time are drawing energy out of the rods 278 and dissipating it through the heat sinks 298 thus allowing the vaporized sterilant to recondense on the rods 278.

The temperature of the inlet manifold 252 can be controlled to slowly vaporize the sterilant thus allowing the water to more quickly vaporize and flow through the vaporizer 250 and out through the orifice 308 to concentrate the remaining sterilant. The condenser/revaporization section 254 quite effectively concentrates the sterilant such that to speed up the process a fast vaporization in the inlet manifold can be employed while still achieving a high degree of concentration.

The condensate on the rods 278 tends to be more highly concentrated in the sterilant. After a time, when the initial charge of sterilant solution has been vaporized and a portion thereof condensed on to the rods 278, the thermo-electric devices 270 and 272 are reversed to apply heat to the rods 278 and revaporize the sterilant. At this time, the heat sink 298 will still contain heat which had been extracted during the prior step and that heat can be used by the thermo-electric devices 270 and 272 to very efficiently heat the rods 278 and revaporize the sterilant. This added efficiency improves the energy efficiently of the device and allows a smaller and more compact vaporize condenser 250 to provide adequate heating and cooling. After the sterilant has been revaporized, the valve 306 is opened to allow efficient diffusion of the sterilant vapor into the main chamber 200.

If a second vaporizer/condenser 216 is employed, its structure preferably mimics that of the vaporizer/condenser 250 without the inlet manifold 252. In such a system, after initial diffusion into the main chamber 200, rods within the second condenser 216 would be chilled and the pump 214 turned on to preferably extract water vapor from the condensing sterilant. After a period of time when sterilant has condensed, the rods would be heated to revaporize the sterilant and the pump 214 turned off. This revaporized sterilant would have somewhat higher concentration and would then re-diffuse into the chamber 200 to further enhance the sterilization process.

Figure 16:
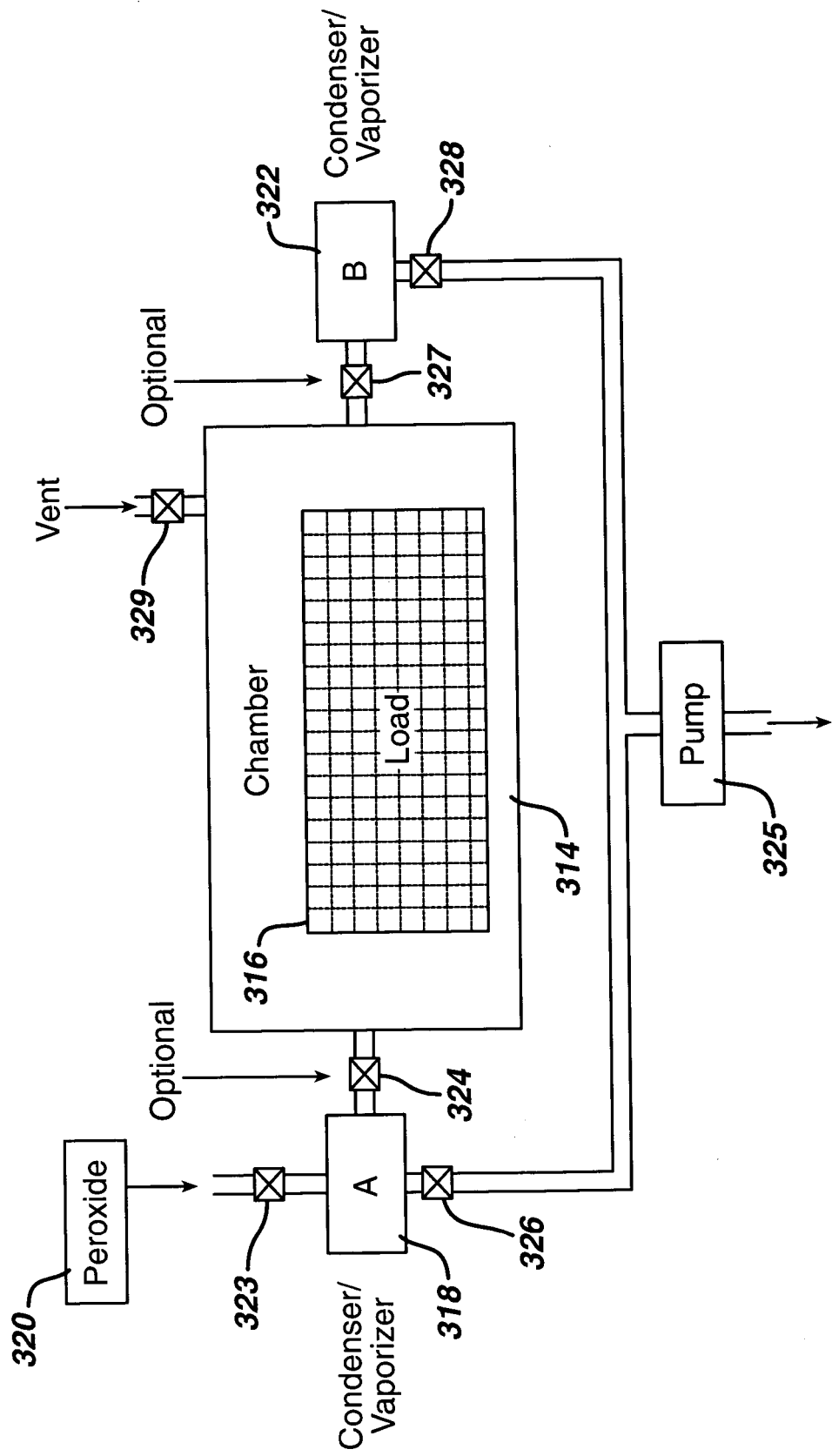
FIG. 16 is an alternative sterilization system according to the present invention.

Other system arrangements are possible. FIG. 16 illustrates an alternative embodiment which can enhance efficiency in conserving and concentrating the germicide solution. In this system, a chamber 314 containing a load 316 has a first condenser/vaporizer 318 connected to a source 320 of germicide solution and a second condenser/vaporizer 322. The first condenser vaporizer 318 is isolated from the source 320 by a valve 323 and from the chamber 314 by a valve 324. It also connects to an exhaust pump 325 and is isolated therefrom via a valve 326. The second condenser vaporizer 322 is isolated from the chamber 314 by a valve 327 and connects to the pump 325 and is isolated therefrom via a valve 328. A vent 329 is also provided.

Figure 17:
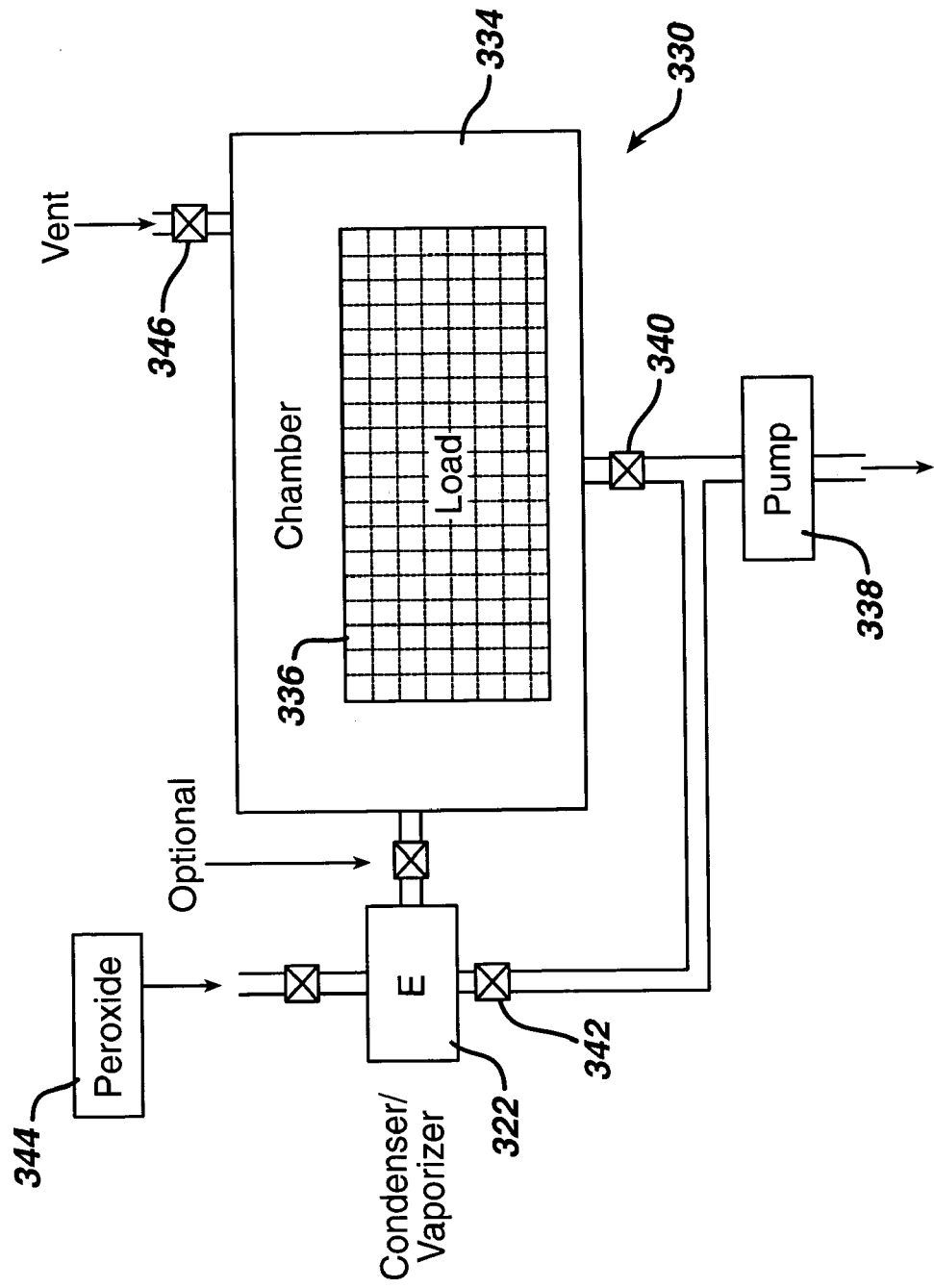
FIG. 17 is an alternative sterilization system according to the present invention.

FIG. 17 illustrates a similar system 330 employing a single condenser/vaporizer 332 (of structure similar to the condenser/vaporizer 250 with an additional outlet) connected to a sterilization chamber 334 adapted to receive a load 336 of instruments to be sterilized. A vacuum pump 338 connects to the chamber 334 via a valve 340 and to the condenser/vaporizer 332 via a valve 342. A three-way valve may substitute for valves 340 and 342. A source of germicidal solution 344 connects to the condenser/vaporizer 332 and the chamber 334 has a vent 346. During initial vaporization and concentration of germicide from the source 344, valve 342 is closed. After the vapor is diffused into the chamber 334, valve 340 can be closed and the pump 338 used to draw vapor out of the chamber through the condenser/vaporizer 332 in its condensing mode to further concentrate the germicide. The concentrated germicide is then revaporized and diffused back into the chamber 334.

The second condenser/vaporizer 216 of FIG. 9 can be used to maximize germicide utilization when running a sterilization process with two full cycles of vacuum, inject, diffuse and vent. Prior to venting during the first cycle, the pump 214 is run with the condenser/vaporizer 216 being chilled to condense the germicide therein. The valves 220 and 218 are closed during the venting process. During the subsequent pump down, the condenser/vaporizer is kept chilled to keep the germicide from unduly vaporizing and being carried out of the system.

The systems of FIGS. 16 and 17 allow even more of the germicide to be retained between cycles in a two cycle process. Prior to venting in the first cycle germicide is condensed into the condenser/vaporizer 332. However, during the subsequent pump down it can be isolated from the pump via the valve 342 thus minimizing the tendency of the pump 338 to pump the saved germicide out of the system during pump down.

In each of this type of system the steps of condensing and concentrating the vaporized germicide and then revaporizing it can be repeated as needed to further concentrate the germicide.

Figure 18:
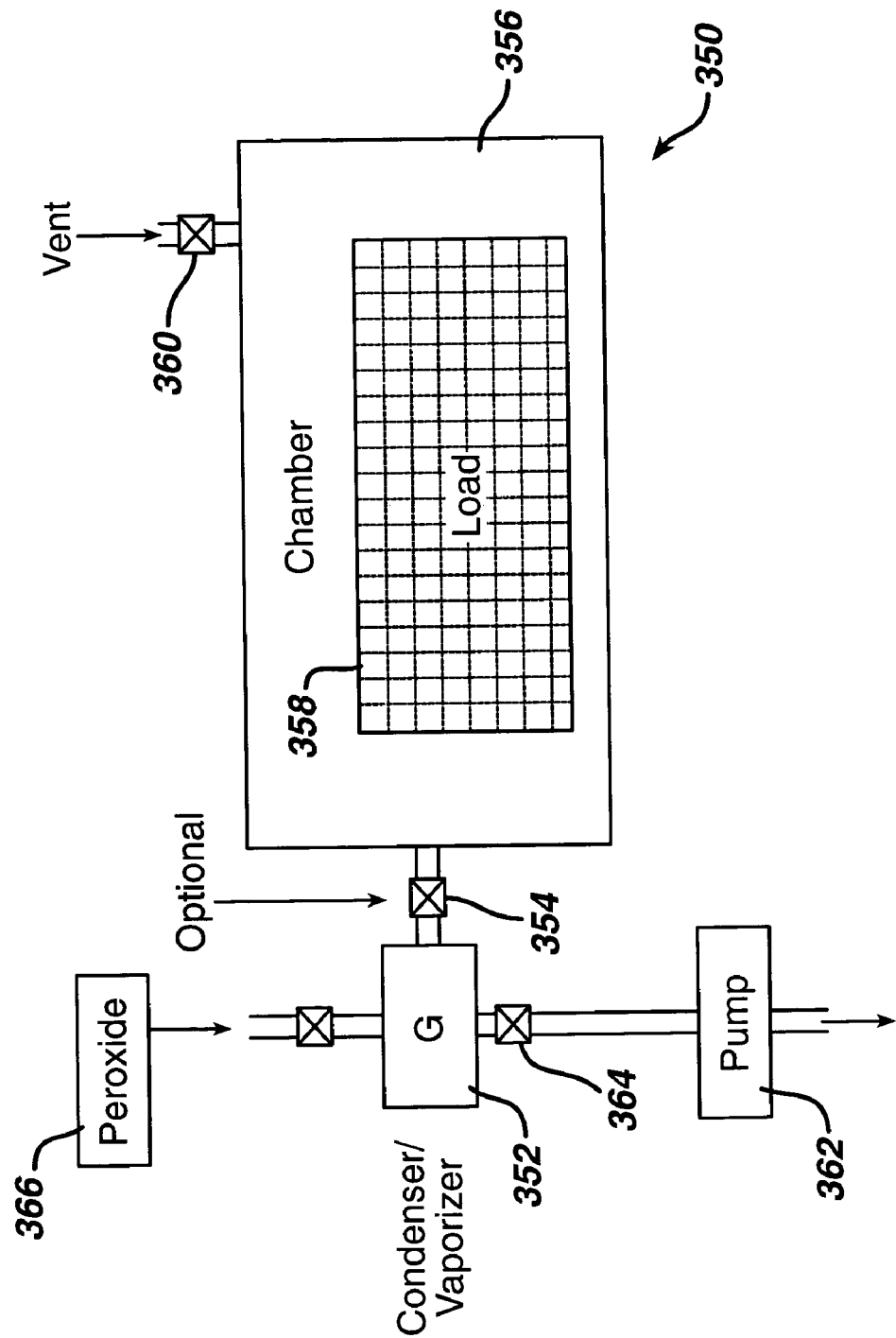
FIG. 18 is an alternative sterilization system according to the present invention.

FIG. 18 illustrates a system 350 plumbed in an alternative fashion. In this system 350 a condenser/vaporizer 352 connects through a valve 354 to a sterilization chamber 356 adapted to receive a load 358 and having a vent 360. A vacuum pump 362 connects to the condenser/vaporizer 352 through a valve 364, but has no separate connection to the chamber 356. A source 366 of germicide connects to the condenser/vaporizer 352.

Figure 19:
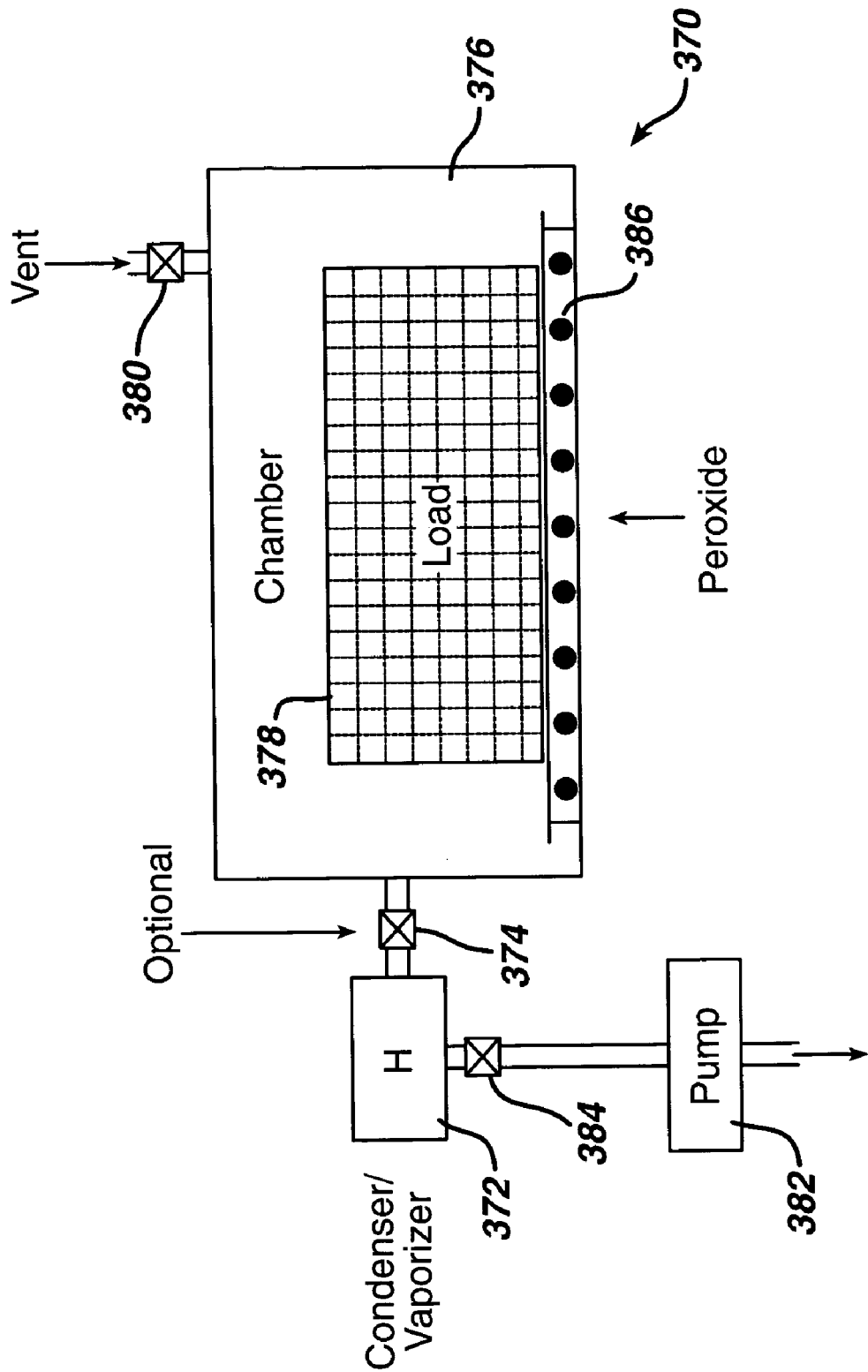
FIG. 19 is an alternative sterilization system according to the present invention.

FIG. 19 illustrates a system 370 plumbed as in FIG. 17, having a condenser/vaporizer 372 which connects through a valve 374 to a sterilization chamber 376 adapted to receive a load 378 and having a vent 380. A vacuum pump 382 connects to the condenser/vaporizer 372 through a valve 384, but has no separate connection to the chamber 356. Rather than an inlet for germicide through the condenser/vaporizer 382, a source 386 of germicide solution is provided within the chamber 376. The source can be simple such as a well containing a quantity of liquid germicide solution. Preferably, it is covered with a semi-permeable membrane or filter so that liquid germicide can not be accidentally spilled therefrom yet as the germicide vaporizes under low chamber pressures the vapors thus generated can pass through the membrane into the chamber. In both systems the condenser/vaporizer 352 or 372 concentrates the germicide via condensation and revaporization of germicide vapor as described above.

Figure 20:
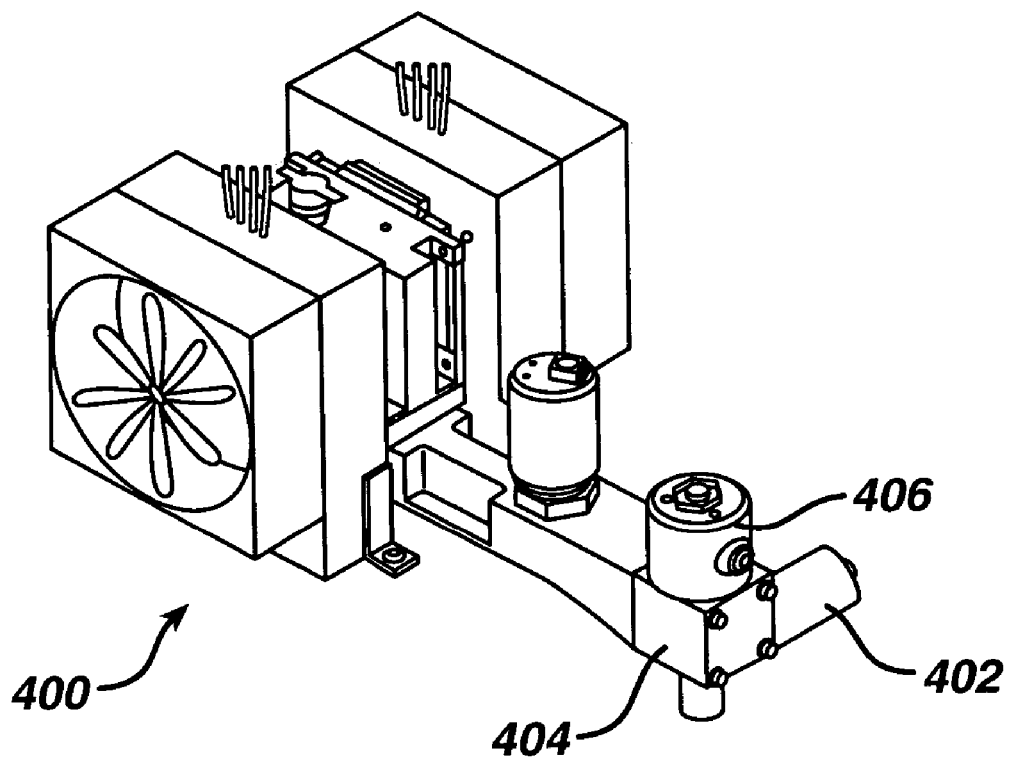
FIG. 20 is a perspective view of an alternative inlet condenser/vaporizer for use in the system of FIG. 9.

FIG. 20 illustrates a further embodiment of an inlet condenser/vaporizer 400. It is similar in most respects to that illustrated in FIG. 12. However, as shown primarily in FIGS. 21 and 22, it features an orifice control valve 402. A valve block 404 receives an outlet control valve 406, a rupture disk 408 and the orifice control valve 404.

Figure 21:
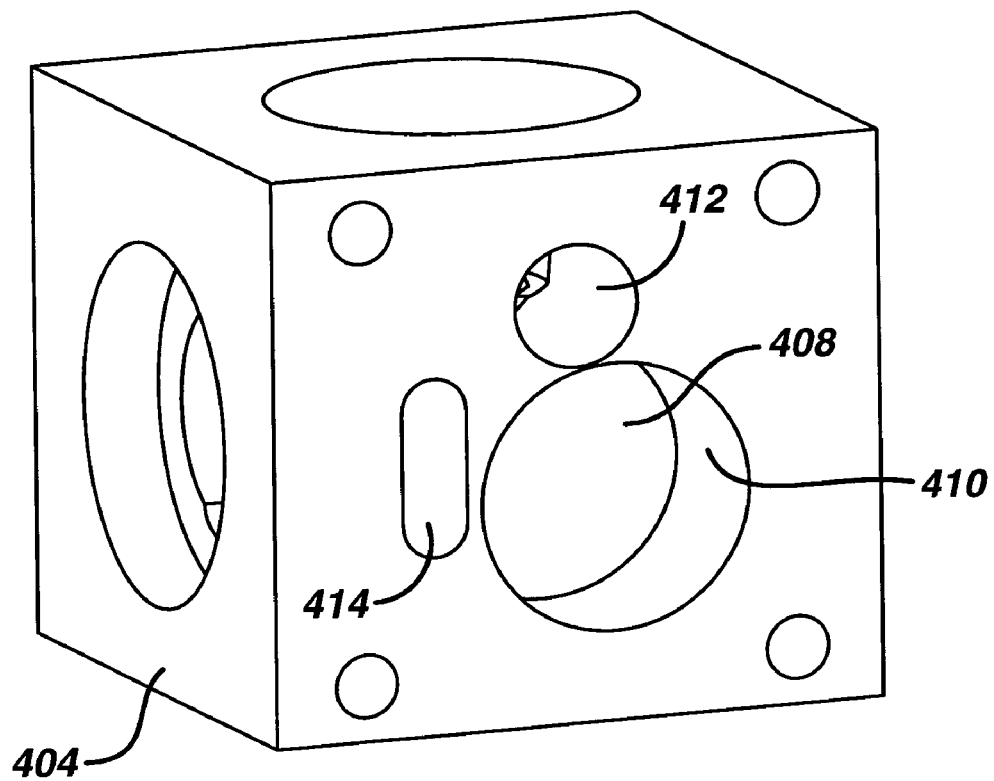
FIG. 21 is a valve block employed in the inlet condenser/vaporizer of FIG. 20.

FIG. 21 shows the valve block 404 in isolation and illustrates three manifold passages which connect the valve block 404 to the rest of the condenser/vaporizer 400: a large pressure relief manifold passage 410 which leads to the rupture disk 408, a smaller upper manifold passage 412 which leads to the outlet control valve 406 and a smaller lateral manifold passage 414 which leads to an orifice 416 and the orifice control valve 402.

Figure 22:
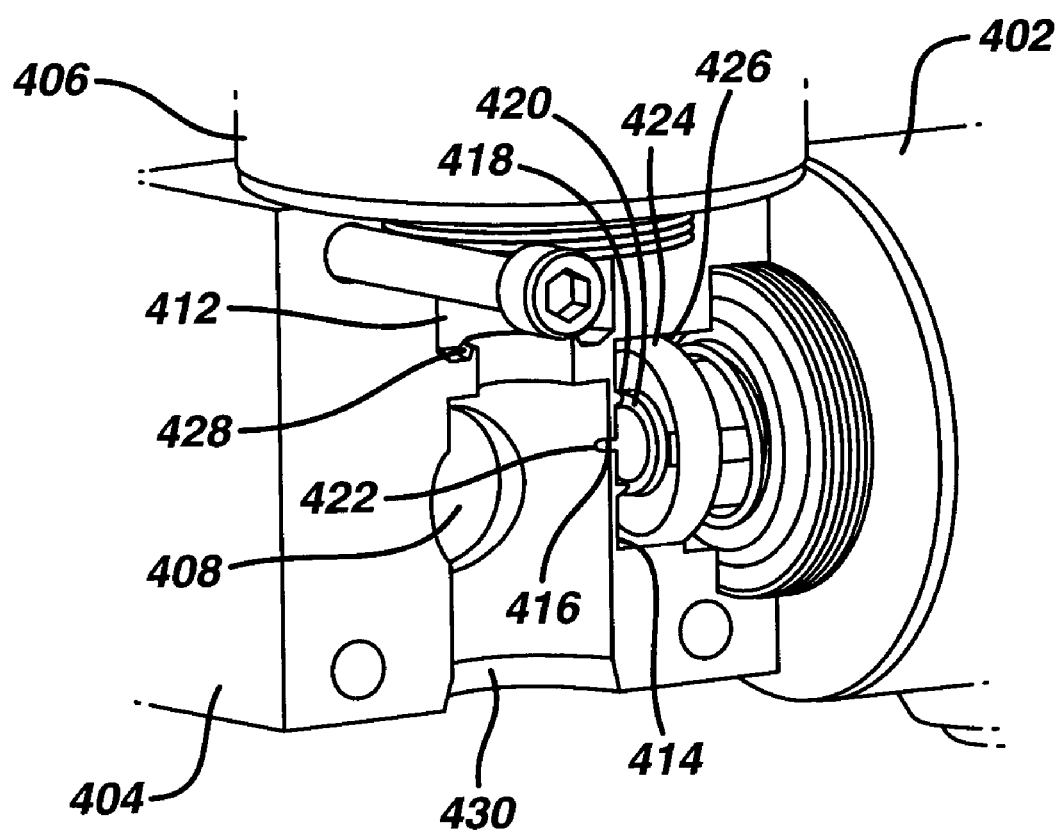
FIG. 22 is a cut-away view of the valve block of FIG. 21 as employed in the inlet condenser/vaporizer of FIG. 20.

FIG. 22 best illustrates the orifice control valve 402. A valve seat 418 on the valve block 404 surrounds the orifice 416. A valve member 420 on the orifice control valve 402 can extend toward to valve seat 418 to seal against it and block fluid communication through the orifice 416. A cleaning pin 422 penetrates the orifice 416 when the orifice control valve 402 is closed to clean the orifice 416 and keep it clear of foreign matter. An annular guide 424 connected to the valve member 420 slides within a bore 426 within the valve block 404 to properly align the cleaning pin 422 with the orifice 416. This view also illustrates a valve seat 428 for the outlet control valve 406 and a valve block outlet passage 430 which leads to the sterilization chamber (not shown in FIGS. 20 to 22).

Operation of a sterilization cycle proceeds nearly the same as afore-described regarding the system shown in FIGS. 12 to 15. However, after the initial vaporization of the sterilant in the inlet manifold 252 (see FIG. 14) the orifice control valve 402 is closed thereby isolating the condenser/vaporizer 400 from the sterilization chamber (not shown in FIGS. 20 to 22). This condition can be monitored most easily be monitoring the pressure within the vaporizer/condenser 400 and assuming that when a particular pressure has been reached that essentially all of the sterilant has been vaporized. Pressure in the sterilization chamber is then reduced, preferably to approximately 0.5 Torr. The outlet control valve 406 is then opened and the rods 278 (see FIG. 14) are heated to vaporize condensed sterilant and pass it through the outlet control valve 406 and outlet passage 430 to the sterilization chamber.

By lowering the pressure in the sterilization chamber prior to admitting the bulk of the sterilant it has been found that overall cycle times may be reduced. Closing the orifice control valve 402 and reducing pressure in the sterilization chamber takes additional time. However, the lower pressure provides a more favorable condition for diffusion of the sterilant into diffusion restricted areas, such as lumens, of instruments to be sterilized. It has been found that the time saved through the increased diffusion efficiency can more than offset the time lost in lowering the pressure in the sterilization chamber. Sterilization cycle speed is an important factor for sterilizer users.

Water vapor in the sterilization chamber can affect time required to lower the pressure therein. Such water vapor typically arises from a load of instruments that have not been properly dried. If undue time is required to remove the water vapor it can be indicated to the user so that they can be reminded to be more vigilant in drying the load for future cycles. There may exist loads of water vapor for which it may take too long to withdraw or to withdraw effectively. In such case the cycle should be cancelled and the user informed as to why.

Table 2 shows control points for three different cycles—a flash or very quick cycle having no lumens, a short cycle having only lumens which present a mild challenge and a long cycle for sterilizing devices with more challenging long and narrow lumens. During an initial pump-down to remove air from the sterilization chamber and vaporizer/condenser 400 the outlet control valve 406 is left open. As the pressure reaches P1 the outlet control valve 406 is closed but the orifice control valve 402 is left open; this starts the vaporization and concentration of the sterilant. Upon reaching pressure P2 within the vaporizer/condenser 400 the pressure Pc within the chamber is checked. If it is above the value listed in Table 2 then the orifice control valve 402 is closed and pump-down continues until Pc is reached and then the outlet control valve 406 is opened to transfer the sterilant into the sterilization chamber. Otherwise, the outlet control valve 406 is opened right away. If the chamber pressure exceeds Pc-cancel at the time that the vaporizer/condenser pressure reaches P2 it is assumed that the sterilization chamber contains too much water and the cycle is cancelled.

TABLE 2

Examples of temperature and pressure set points

| Load condition | Flash Surface | Short<br>1 mm × 150 mm SS<br>1 mm × 350 mm<br>Plastic | Long<br>1 mm × 500 mm SS<br>1 mm × 1000 mm<br>Plastic |
|---|---|---|---|
| Vaporizer temperature | 70° C. | 70° C. | 70° C. |
| Condenser temperature | 58° C. | 52° C. | 43° C. |
| P1 Vaporizer/condenser pressure to remove air | 140 torr | 140 torr | 140 torr |
| P2 Vaporizer/condenser pressure to concentrate sterilant | 22 torr | 16 torr | 10 torr |
| Pc Chamber pressure to select transfer, additional vacuum or cancellation | 1.5 torr | 0.6 torr | 0.3 torr |
| Pc-cancel Chamber pressure to cancel cycle | 8 torr | 6 torr | 4 torr |
| Condenser temperature to transfer concentrated sterilant | 68° C. | 68° C. | 68° C. |

Figure 23:
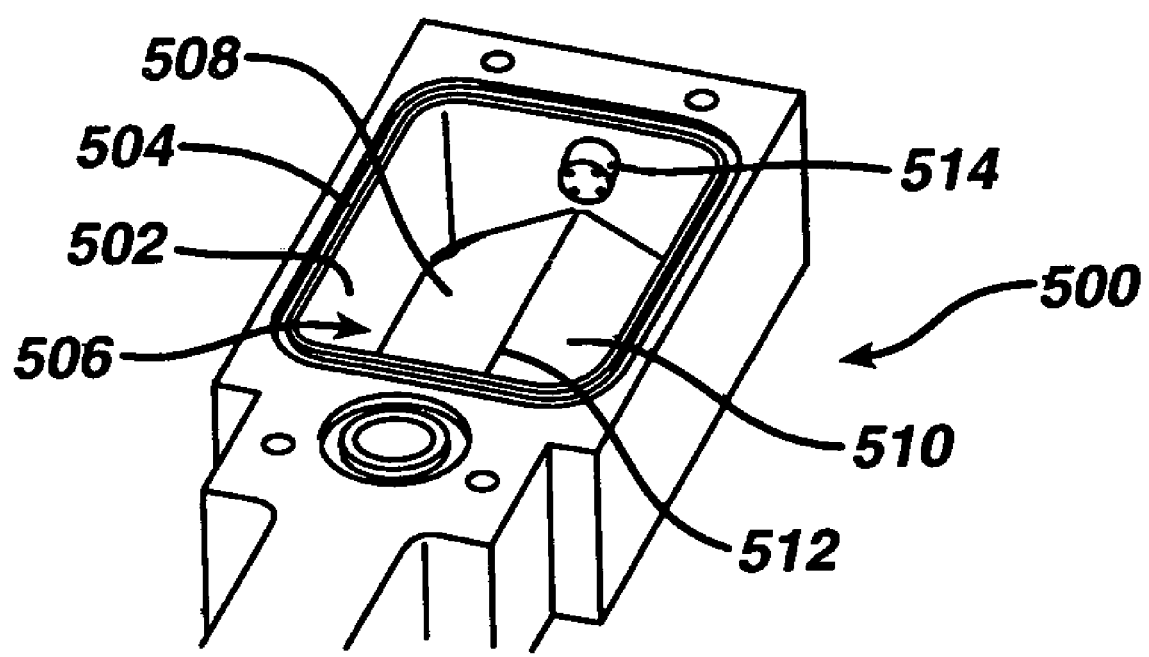
FIG. 23 is a perspective view of a vaporizer according to the present invention.

FIG. 23 illustrates an alternative vaporizer 500 according to the present invention. It comprises a cavity 502 open at an upper extent 504 for connection to the condensing/revaporization section 254 (see also FIG. 14) and having a lower vaporizing surface 506. The vaporizing surface 506 comprises a first face 508 and second face 510 inclined toward each other to join at a ridge 512. The vaporizing surface can be formed integrally with the cavity 502 or be a separate part which fits therein. An inlet 514 provides liquid sterilant solution, such as a solution of hydrogen peroxide and water, to the vaporizing surface 506.

The inlet 514 can take several forms. Preferably it showers droplets of liquid sterilant solution evenly over the ridge 512, allowing the droplets to flow down the first and second faces 508 and 510 thereby evenly distributing vaporization over the vaporizing surface 506. It can comprise multiple nozzles or openings distributed above the ridge 512. Each nozzle could comprise multiple openings. Even distribution promotes more rapid vaporization which can lower the time to complete a sterilization cycle. It also promotes uniformity in vaporization to maintain synchronicity with the condensing and revaporization.

The sloping faces 508 and 510 also economize space and enhance vaporization by enhancing the surface area to volume ratio for a given footprint, simultaneously promoting even distribution of liquid sterilant solution over the vaporizing surface 506. Preferably, the first face and second face 508 and 510 are inclined between 15 to 60 degrees with respect to horizontal, and more preferably 25 to 50 degrees.

The vaporizing surface 506 can be configured to promote an even distribution of flow over it. For instance it can be textured, or provided with flow enhancing grooves, preferably vertically oriented. It can also be provided with a plurality of small pockets which catch a small amount of the liquid sterilant as it flows over the vaporizing surface 506 thereby evenly distributing the vaporization. Preferably, each pocket traps about ten to fifty micro liters of sterilant solution. In one aspect of the invention the total amount of sterilant would be 1.8 ml of 59% hydrogen peroxide solution.

The vaporizing surface 506 can also be covered with protrusions to increase its surface area. A surface of densely packed half-spheres would increase the surface area by about 78%. The additional surface area promotes more rapid vaporization of the liquid sterilant solution.

In addition to the triangular prism shape of the vaporizing surface 506 shown, other shapes would achieve a similar goal. For instance, the vaporizing surface could comprise an outer surface of a vertical cone, a pyramid or a half-sphere.

While described in connection with the condensing/re-vaporization section 254 and other equipment to concentrate sterilization vapors, the vaporizer 500 would similarly enhance a more typical vapor phase sterilization system in which the liquid sterilant solution is vaporized and fed directly into a sterilization chamber without attempts at concentration thereof.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A method of providing a vapor phase sterilant solution to a sterilization chamber, the method comprising the steps of:
   providing a vaporizer comprising a cavity;
   providing a first inclined face extending in a first direction and a second inclined face extending in a second direction which is different than the first direction, wherein the first and second inclined faces are arranged to form an elongate ridge therebetween, the elongate ridge comprising:
      a first end positioned adjacent to a first sidewall of the cavity; and
      a second end positioned adjacent to a second sidewall of the cavity;
   providing a nozzle positioned on the first sidewall, wherein the nozzle comprises an opening defined therein;
   showering a liquid sterilant solution from the opening, wherein the liquid sterilant solution travels from the opening in a direction along a portion of the elongate ridge from the first end toward the second end;
   flowing the liquid sterilant solution over the first inclined face;
   flowing the liquid sterilant solution over the second inclined face;
   vaporizing the liquid sterilant solution flowing over the first and second inclined faces to form the vapor phase sterilant solution; and
   transferring the vapor phase sterilant solution to the sterilization chamber.

2. The method according to claim 1, wherein the nozzle comprises a multiple-stream nozzle, and wherein the step of showering the liquid sterilant solution includes spraying the liquid sterilant solution along the portion of the elongate ridge using a multiple-stream nozzle.

3. The method according to claim 1, further comprising the steps of:
   capturing a volume of the liquid sterilant solution flowing over the first inclined face in a plurality of wells defined in the first inclined face; and
   holding the volume of the liquid sterilant solution in the plurality of wells until the volume is vaporized.

4. The method according to claim 1, wherein the nozzle comprises a plurality of openings, the method further comprising the step of:
   positioning the nozzle laterally relative to the elongate ridge such that at least one opening is situated on a first side of the elongate ridge and at least one opening is situated on a second side of the elongate ridge.

5. The method according to claim 1, wherein the first inclined face includes a first lower end, and wherein the second inclined face includes a second lower end, the method further comprising the steps of:
   providing a first upwardly-extending wall extending from the first lower end and a second upwardly-extending wall extending from the second lower end; and
   flowing the liquid sterilant solution toward the first and second upwardly-extending walls.

6. The method according to claim 1, wherein the first inclined face includes a plurality of channels, the method further comprising the step of flowing the liquid sterilant solution within the channels.

7. The method according to claim 1, wherein the elongate ridge is provided in a substantially horizontal orientation.

8. A method of providing a vapor phase sterilant solution to a sterilization chamber, the method comprising the steps of:
   providing a vaporizer comprising a cavity;
   providing a first inclined face and a second inclined face, wherein the first and second inclined faces are arranged to form an elongate ridge therebetween, the elongate ridge comprising:
      a first end situated next to a first sidewall of the cavity; and
      a second end situated next to a second sidewall of the cavity;
   providing a nozzle positioned on the first sidewall, wherein the nozzle comprises an opening defined therein;
   projecting a liquid sterilant solution from the opening, wherein the liquid sterilant solution is projected from the opening in a direction substantially along a portion of the elongate ridge from the first end toward the second end;
   flowing the liquid sterilant solution over the first inclined face;
   flowing the liquid sterilant solution over the second inclined face;
   vaporizing the liquid sterilant solution to form the vapor phase sterilant solution; and
   transferring the vapor phase sterilant solution to the sterilization chamber.

9. A method of providing a vapor phase sterilant solution to a sterilization chamber, the method comprising the steps of:
   providing a vaporizer comprising a cavity;
   wherein the vaporizer comprises a vaporizing surface comprising:
      a crown;
      a first surface extending downwardly from the crown in a first direction; and a second surface extending downwardly from the crown in a second direction, wherein the first direction is different than the second direction, the crown comprising:
- a first end portion situated next to a first sidewall of the cavity; and
- a second end portion situated next to a second sidewall of the cavity;

providing a nozzle positioned on the first sidewall, wherein the nozzle comprises an opening defined therein;

showering a liquid sterilant solution from the opening, wherein the liquid sterilant solution is projected from the opening in a direction substantially along a portion of the crown from the first end toward the second end;

flowing the liquid sterilant solution over the first downwardly-extending surface;

flowing the liquid sterilant solution over the second downwardly-extending surface;

vaporizing the liquid sterilant solution to form the vapor phase sterilant solution; and transferring the vapor phase sterilant solution to the sterilization chamber.

10. A method of providing a vapor phase sterilant solution to a sterilization chamber, the method comprising the steps of:
providing a vaporizer comprising a chamber
wherein the vaporizer comprises a vaporizing surface comprising:
- a crest comprising:
  - a first end attached to a first sidewall of the chamber; and
  - a second end attached to a second sidewall of the chamber;
- a first surface extending downwardly from the crest in a first direction; and
- a second surface extending downwardly from the crest in a second direction; wherein the first direction is different than the second direction;

providing an inlet on the first sidewall, wherein the inlet comprises an opening defined therein;

projecting a liquid sterilant solution from the opening, wherein the liquid sterilant solution is projected from the opening near the first end of the crest toward the second end of the crest;

flowing the liquid sterilant solution over the first downwardly-extending surface;

flowing the liquid sterilant solution over the second downwardly-extending surface;

vaporizing the liquid sterilant solution to form the vapor phase sterilant solution; and transferring the vapor phase sterilant solution to the sterilization chamber.

11. The method according to claim 10, further comprising the steps of:
capturing a volume of the liquid sterilant solution flowing over the first downwardly-extending surface in a plurality of wells defined in the first downwardly-extending surface; and
holding the volume of the liquid sterilant solution in the plurality of wells until the volume is vaporized.

12. The method according to claim 10, wherein the first downwardly-extending surface includes a first lower end, and wherein the second downwardly-extending surface includes a second lower end, the method further comprising the steps of:
providing a first upwardly-extending wall extending from the first lower end and a second upwardly-extending wall extending from the second lower end; and
flowing the liquid sterilant solution toward the first and second upwardly-extending walls.

* * * * *